United States Patent
Burns et al.

(10) Patent No.: US 12,187,752 B2
(45) Date of Patent: *Jan. 7, 2025

(54) SOLID FORMS AND COMBINATION COMPOSITIONS COMPRISING A BETA-LACTAMASE INHIBITOR AND USES THEREOF

(71) Applicant: Venatorx Pharmaceuticals, Inc., Malvern, PA (US)

(72) Inventors: Christopher J. Burns, Malvern, PA (US); Daniel C. Pevear, Downingtown, PA (US); Luigi Xerri, Wayne, PA (US); Timothy Henkel, Berwyn, PA (US); Daniel McGarry, Malvern, PA (US); Lawrence Rosen, Malvern, PA (US); Gerald Brenner, Plymouth, PA (US); Jean-Baptiste Arlin, Amsterdam (NL); Ana Fernandez Casares, Amsterdam (NL)

(73) Assignee: VENATORX PHARMACEUTICALS, INC., Malevern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/476,050

(22) Filed: Sep. 27, 2023

(65) Prior Publication Data

US 2024/0101580 A1    Mar. 28, 2024

Related U.S. Application Data

(60) Continuation of application No. 17/353,377, filed on Jun. 21, 2021, now Pat. No. 11,820,784, which is a division of application No. 16/491,116, filed as application No. PCT/US2018/020968 on Mar. 5, 2018, now Pat. No. 11,091,505.

(60) Provisional application No. 62/564,989, filed on Sep. 28, 2017, provisional application No. 62/564,990, filed on Sep. 28, 2017, provisional application No. 62/467,752, filed on Mar. 6, 2017, provisional application No. 62/467,750, filed on Mar. 6, 2017.

(51) Int. Cl.
| | | |
|---|---|---|
| *A61P 31/04* | (2006.01) | |
| *A61K 9/00* | (2006.01) | |
| *A61K 31/546* | (2006.01) | |
| *A61K 31/69* | (2006.01) | |
| *A61K 47/02* | (2006.01) | |
| *A61K 47/12* | (2006.01) | |
| *A61K 47/18* | (2017.01) | |
| *A61K 47/26* | (2006.01) | |
| *C07F 5/02* | (2006.01) | |

(52) U.S. Cl.
CPC ............ *C07F 5/027* (2013.01); *A61K 9/0095* (2013.01); *A61K 47/02* (2013.01); *A61K 47/12* (2013.01); *A61K 47/183* (2013.01); *A61K 47/26* (2013.01); *A61P 31/04* (2018.01); *A61K 9/0019* (2013.01); *A61K 31/546* (2013.01)

(58) Field of Classification Search
CPC .......... C07F 5/027; C07F 5/025; A61P 31/04; A61K 9/0095; A61K 9/0019; A61K 47/02; A61K 47/12; A61K 47/183; A61K 47/26; A61K 31/546; A61K 31/69
See application file for complete search history.

(56) References Cited

U.S. PATENT DOCUMENTS

| | | |
|---|---|---|
| 7,271,186 B1 | 9/2007 | Shoichet et al. |
| 7,714,159 B2 | 5/2010 | Pickersgill et al. |
| 8,283,467 B2 | 10/2012 | Ammoscato et al. |
| 8,912,169 B2 | 12/2014 | Burns et al. |
| 9,040,504 B2 | 5/2015 | Burns et al. |
| 9,376,454 B2 | 6/2016 | Burns et al. |
| 9,403,850 B2 | 8/2016 | Burns et al. |
| 9,422,314 B2 | 8/2016 | Burns et al. |
| 9,637,504 B2 | 5/2017 | Burns et al. |
| 9,771,382 B2 | 9/2017 | Burns et al. |
| 9,828,391 B2 | 11/2017 | Burns et al. |
| 10,214,547 B2 | 2/2019 | Burns et al. |
| 10,669,290 B2 | 6/2020 | Burns et al. |
| 10,889,600 B2 | 1/2021 | Amann et al. |
| 11,091,505 B2 | 8/2021 | Burns et al. |
| 11,560,392 B2 | 1/2023 | Amann et al. |
| 11,820,784 B2 | 11/2023 | Burns et al. |
| 2009/0156518 A1 | 6/2009 | Zhang |
| 2010/0120715 A1 | 5/2010 | Burns et al. |
| 2010/0286092 A1 | 11/2010 | Burns et al. |
| 2010/0292185 A1 | 11/2010 | Burns et al. |
| 2010/0317621 A1 | 12/2010 | Burns et al. |

(Continued)

FOREIGN PATENT DOCUMENTS

| | | |
|---|---|---|
| CN | 1965838 A | 5/2007 |
| CN | 105801610 A | 7/2016 |

(Continued)

OTHER PUBLICATIONS

Bacterial Infection 101. Available at http://www.onhealth.com/content/l/bacterial_infections (34 pgs) (2017).
Bundgaard. Design of Prodrugs. Elsevier. Chapter 1. pp. 1-3 (1985).
Burns et al. , Accession No. 2014:955904. STN International CAPLUS database, (Columbus, Ohio) (2014).
Burns et al. CAPLUS AN 2014-1130723 (1 pg.) (2014).
Byrn et al. Pharmaceutical Solids: A Strategic Approach to Regulatory Considerations. Pharm Res 12(7):945-954 (1995).
Cho et al. A practical synthesis of enantiopure 4,4,4-trifluoro-allo-threonine from an easily available fluorinated building block. Tetrahedron Lett. 56:127-131 (2015).

(Continued)

*Primary Examiner* — Sun Jae Yoo
(74) *Attorney, Agent, or Firm* — WILSON SONSINI GOODRICH & ROSATI

(57) ABSTRACT

Described herein are crystalline forms of (R)-3-(2-(trans-4-(2-aminoethylamino)cyclohexyl)acetamido)-2-hydroxy-3,4-dihydro-2H-benzo[e][1,2]oxaborinine-8-carboxylic acid. In some embodiments, the crystalline forms are formulated for treating a subject in need thereof with a bacterial infection.

15 Claims, 15 Drawing Sheets

(56) References Cited

U.S. PATENT DOCUMENTS

| | | |
|---|---|---|
| 2011/0294777 A1 | 12/2011 | Blizzard et al. |
| 2012/0040932 A1 | 2/2012 | Hirst et al. |
| 2014/0171390 A1* | 6/2014 | Burns ............... A61K 9/0019 546/13 |
| 2014/0194385 A1 | 7/2014 | Reddy et al. |
| 2014/0194386 A1 | 7/2014 | Burns et al. |
| 2015/0094472 A1 | 4/2015 | Hecker et al. |
| 2015/0361107 A1 | 12/2015 | Trout |
| 2017/0073360 A1 | 3/2017 | Burns et al. |
| 2017/0281639 A1 | 10/2017 | Kawasaki et al. |
| 2018/0002351 A1 | 1/2018 | Hecker et al. |
| 2022/0054513 A1 | 3/2022 | Hamrick et al. |

FOREIGN PATENT DOCUMENTS

| | | |
|---|---|---|
| JP | 2015508801 A | 3/2015 |
| KR | 20130064004 A | 6/2013 |
| RU | 2445314 C9 | 4/2013 |
| WO | WO-2005097809 A2 | 10/2005 |
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2012021455 A1 | 2/2012 |
| WO | WO-2013014497 A1 | 1/2013 |
| WO | WO-2013053372 A1 | 4/2013 |
| WO | WO-2013122888 A2 | 8/2013 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2015157618 A1 | 10/2015 |
| WO | WO-2015191907 A1 | 12/2015 |
| WO | WO-2016100043 A1 | 6/2016 |
| WO | WO-2018027062 A1 | 2/2018 |
| WO | WO-2018165048 A1 | 9/2018 |
| WO | WO-2019226931 A1 | 11/2019 |
| WO | WO-2020056048 A1 | 3/2020 |
| WO | WO-2020112542 A1 | 6/2020 |

OTHER PUBLICATIONS

Choi et al. Cefiderocol: a novel siderophore cephalosporin. Expert Opin Investig Drugs 27(2):193-197 (2018).
Deng et al. Dynamic pharmacophore model optimization: identification of novel HIV-1 integrase inhibitors. J Med Chem 49:1684-1692 (2006).
Eidam et al. Design, synthesis, crystal structures, and antimicrobial activity of sulfonamide boronic acids as β-lactamase inhibitors. J. Med. Chem. 53(21):7852-7863 (2010).
Georgiou et al. VNRX-5133, a novel broad-spectrum beta-lactamase inhibitor, enhances the activity of cefepime against resistant Enterobacteriaceae and P. aeruginosa isolates in a neutropenic mouse-thigh infection model. European Congress of Clinical Microbiology and Infectious Diseases, Apr. 24, 2018 (Apr. 24, 2018 Retrieved from the Internet: URL:https://www.escmid.org/escmid_publications/escmid_elibrary/.
Germs: Understand and protect against bacteria, viruses and infection, PreventBacterialInfection, 2020. Available at https://www.mayoclinic.org/diseases-conditions/infectious-diseases/in-depth/germs/art-20045289#:-:text=Warding%20off%20germs%20and%20infection&text=You%20can%20prevent%20infections%20through ,vaccinations%2C%20and%20taking%20appropriate%20medications (Mar. 5, 2020).
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Hardy et al. The Chemistry of Some 2-Aminothiazol-4-ylacetic Acid Derivatives and the Synthesis of Derived Penicillins. J Chem Soc Perkin Trans 1:1227-1235 (1984).

Higgins et al. In Vitro Activities of the -Lactamase Inhibitors Clavulanic Acid, Sulbactam, and Tazobactam Alone or in Combination with -Lactams against Epidemiologically Characterized Multidrug-Resistant Acinetobacter baumannii Strains. Antimicron Agents Chemother 48(5):1586-1592 (2004).
ISOMER. https://en.wikipedia.org/wiki/lsomer (5 pgs.) (2015).
ISOMER. https://en.wikipedia.org/wiki/Isomer (5 pgs) (2017).
Katsube et al. Cefiderocol, a Siderophore Cephalosporin for Gram-Negative Bacterial Infections: Pharmacokinetics and Safety in Subjects With Renal Impairment. J Clin Pharmacol 57(5):584-591 (2017).
King et al. Molecular Mechanism of Avibactam-Mediated β-Lactamase Inhibition. ACS Infect Dis 1(4):175-84 (2015).
Krajnc et al., Bicyclic boronate VNRX-5133 inhibits metallo- and serine-beta-lactamases. Journal of Medicinal Chemistry 62(18):8544-8556 (2019).
Martin et al. Rational design and synthesis of a highly effective transition state analog inhibitor of the RTEM-1 β-lactamase. Tetrahedron Lett. 36:8399-8402 (1995).
Matteson. Boronic esters in asymmetric synthesis. J Org Chem 78:10009-10023 (2013).
Matteson et al. Synthesis of 1-amino-2-phenylethane-1-boronic acid derivatives. Organometallics 3:614-18 (1984).
Maxipime (Cefepime Hydrochloride, USP) for Injection) Hospira, Inc. Revised Jun. 2012 (24 pgs).
Morandi et al. Structure-based optimization of cephalothin-analogue boronic acids as β-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
PCT/US2013/073428 International Search Report and Written Opinion dated Apr. 25, 2014.
PCT/US2017/045347 International Search Report and Written Opinion dated Nov. 8, 2017.
PCT/US2018/020968 International Search Report and Written Opinion dated Jun. 29, 2018.
PCT/US2019/050682 International Search Report and Written Opinion dated Jan. 3, 2020.
PCT/US2019/062798 International Search Report and Written Opinion dated Jan. 27, 2020.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Prevent Bacterial Infection. https:/Avww.mayoclinic.org/diseases-conditions/infectious-diseases/in-depth/germs/art-20045289#:-:text=Warding%20off%20germs%20and%20infection&text=You%20can%20prevent%20infections%20through ,vaccinations%20% (2020).
Reddy et al. Caplus 2014:1118372 (2014) (2 pgs.).
Shah et al. Chapter 2: Approaches for Improving Bioavailability of Poorly Soluble Drugs. Pharmaceutical Dosage Forms: Tablets. 3rd edition, vol. 2, chapter 2 (Augsburger et al. editors), p. 62-66 (Dec. 31, 2008).
The Chemical Society of Japan (ed.), The Fourth Edition of Lecture Notes in Experimental Chemistry 1: Basic Operations I, pp. 184-189, Published by Maruzen Co., Apr. 5, 1996.
U.S. Appl. No. 14/649,527 Office Action dated Nov. 9, 2015.
U.S. Appl. No. 15/212,959 Office Action dated Mar. 23, 2017.
U.S. Appl. No. 15/797,224 Office Action dated Aug. 13, 2018.
U.S. Appl. No. 16/238,363 Office Action dated Sep. 10, 2019.
U.S. Appl. No. 16/491,116 Office Action dated Dec. 14, 2020.
U.S. Appl. No. 16/491,116 Office Action dated Mar. 25, 2021.
U.S. Appl. No. 17/115,514 Office Action dated Apr. 28, 2022.
U.S. Appl. No. 17/353,377 Office Action dated Feb. 24, 2023.
Weston et al. Structure-based enhancement of boronic acid-based inhibitors of AmpC β-lactamase. J. Med. Chem. 41(23):4577-4586 (1998).

(56) References Cited

OTHER PUBLICATIONS

Hirayama Yoshinaki. Handbook of organic compound crystal—Principle and know-how, Marzen Co., Ltd., p. 57-84 (Jan. 25, 2008).

* cited by examiner

SOLID FORMS AND COMBINATION COMPOSITIONS COMPRISING A BETA-LACTAMASE INHIBITOR AND USES THEREOF

CROSS-REFERENCE

This application is a continuation of U.S. application Ser. No. 17/353,377, filed Jun. 21, 2021, which is a division of U.S. application Ser. No. 16/491,116, filed Sep. 4, 2019, now issued as U.S. Pat. No. 11,091,505, issued on Aug. 17, 2021, which is a U.S. National Stage entry of International Application No. PCT/US2018/20968, filed Mar. 5, 2018, which claims the benefit of U.S. Provisional Application No. 62/467,750, filed Mar. 6, 2017; U.S. Provisional Application No. 62/467,752, filed Mar. 6, 2017, U.S. Provisional Application No. 62/564,989, filed Sep. 28, 2017, and U.S. Provisional Application No. 62/564,990, filed Sep. 28, 2017; each of which is incorporated herein by reference in their entirety.

STATEMENT AS TO FEDERALLY SPONSORED RESEARCH

This invention was made with government support under R43AI096679, R44AI096613, R44AI096679, R43AI096613, and HHSN272201300019C awarded by the National Institutes of Health (NIH) and HHSO100201900007C awarded by the Department of Health and Human Services; Office of the Assistant Secretary for Preparedness and Response, Biomedical Advanced Research and Development Authority. The government has certain rights in the invention.

FIELD OF INVENTION

The present invention relates to pharmaceutical compositions containing boron-containing compounds, polymorphic forms, preparations and their use as inhibitors of beta-lactamase enzymes and as antibacterial agents in combination with a beta-lactam antibiotic.

BACKGROUND OF THE INVENTION

Antibiotics are the most effective drugs for treating bacteria-infectious diseases. They are largely used in the clinic because of their good antibacterial effect with limited side effects. Among them, the beta-lactam class of antibiotics (for example, penicillins, cephalosporins, monobactams and carbapenems) are preferred because their effect is bactericidal and their target is absent in eukaryotic cells with consequent low toxicity.

To counter the efficacy of the various beta-lactams, bacteria have evolved to produce variants of beta-lactam deactivating enzymes called beta-lactamases, and in the ability to share this tool both vertically and horizontally inter- and intra-species. These beta-lactamases are categorized as "serine" or "metallo" based, respectively, based on the presence of a key serine or zinc in the enzyme active site. The rapid induction, selection and spread of this mechanism of bacterial resistance can severely limit the whole class of beta-lactam treatment options in the hospital and in the community. There is a need for effective and safe therapeutic agents that can treat such resistant infections.

SUMMARY OF THE INVENTION

Disclosed herein is a pharmaceutical composition comprising:
(i) (R)-3-(2-(trans-4-(2-aminoethylamino)cyclohexyl)acetamido)-2-hydroxy-3,4-dihydro-2H-benzo[e][1,2]oxaborinine-8-carboxylic acid:

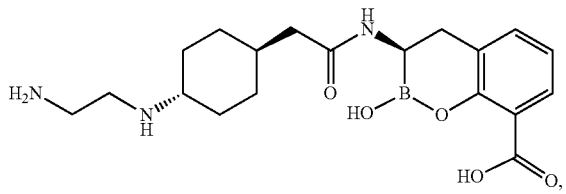 [SMILES: NCCN[C@H]1CC[C@H](CC(=O)N[C@H]2Cc3cccc(C(=O)O)c3OB2O)CC1]

a pharmaceutically acceptable salt, a solvate, or a pharmaceutically acceptable salt and solvate thereof; and
(ii) cefepime.

In some embodiments of a pharmaceutical composition, the pharmaceutical composition is formulated as a homogeneous liquid suitable for injection.

In some embodiments of a pharmaceutical composition, the pharmaceutical composition further comprises a pharmaceutically acceptable excipient.

In some embodiments of a pharmaceutical composition, the pharmaceutically acceptable excipient is an amino acid or a monosaccharide derivative.

In some embodiments of a pharmaceutical composition, the pharmaceutically acceptable excipient is L-arginine.

In some embodiments of a pharmaceutical composition, the pharmaceutically acceptable excipient is meglumine.

In some embodiments of a pharmaceutical composition, the pharmaceutical composition further comprises an aqueous carrier.

In some embodiments of a pharmaceutical composition, the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof.

In some embodiments of a pharmaceutical composition, the pharmaceutical composition has a pH from about 4 to about 9.

In some embodiments of a pharmaceutical composition, the pharmaceutical composition has a pH from about 4 to about 6.

In some embodiments of a pharmaceutical composition, the pharmaceutical composition is formulated as a powder for reconstitution.

In some embodiments of a pharmaceutical composition, the pharmaceutical further comprises a pharmaceutically acceptable excipient.

In some embodiments of a pharmaceutical composition, the pharmaceutically acceptable excipient is an amino acid or a monosaccharide derivative.

In some embodiments of a pharmaceutical composition, the pharmaceutically acceptable excipient is L-arginine.

In some embodiments of a pharmaceutical composition, the pharmaceutically acceptable excipient is meglumine.

In some embodiments of a pharmaceutical composition, the pharmaceutical composition is suitable for injection once reconstituted with an aqueous carrier.

In some embodiments of a pharmaceutical composition, the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof.

In some embodiments of a pharmaceutical composition, the pharmaceutical composition is stable at about 25° C.±2° C./60% RH±5% RH for at least 12 months.

In some embodiments of a pharmaceutical composition, (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof, is crystalline.

In some embodiments of a pharmaceutical composition, crystalline (R)-3-(2-(trans-4-(2-aminoethylamino)cyclohexyl)acetamido)-2-hydroxy-3,4-dihydro-2H-benzo[e][1,2]oxaborinine-8-carboxylic acid is in the form of a dihydrochloride or a solvate thereof.

In some embodiments of a pharmaceutical composition, crystalline (R)-3-(2-(trans-4-(2-aminoethylamino)cyclohexyl)acetamido)-2-hydroxy-3,4-dihydro-2H-benzo[e][1,2]oxaborinine-8-carboxylic acid dihydrochloride is in the form of a monohydrate solvate.

In some embodiments of a pharmaceutical composition, the crystalline form has an X-Ray powder diffraction (XRPD) pattern substantially the same as shown in FIG. 2.

In some embodiments of a pharmaceutical composition, the crystalline form has an X-Ray powder diffraction (XRPD) pattern substantially the same as shown in FIG. 3.

In some embodiments of a pharmaceutical composition, the crystalline form has an X-ray powder diffraction (XRPD) pattern comprising characteristic peaks at about 7.0°±0.1° 2θ, about 14.1°±0.1° 2θ, about 20.2°±0.1° 2θ, about 24.6°±0.1° 2θ, and about 27.7°±0.1° 2θ.

In some embodiments of a pharmaceutical composition, the X-ray powder diffraction (XRPD) pattern further comprises characteristic peaks at about 10.5°±0.1° 2θ, about 18.9°±0.1° 2θ, about 23.7°±0.1° 2θ, about 25.6°±0.1° 2θ, and about 29.6°±0.1° 2θ.

In some embodiments of a pharmaceutical composition, the pharmaceutical composition comprises about 500 mg of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

In some embodiments of a pharmaceutical composition, the pharmaceutical composition comprises about 750 mg of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

In some embodiments of a pharmaceutical composition, the pharmaceutical composition comprises about 2 g of cefepime.

Also disclosed herein is a method of treating a bacterial infection in a subject in need thereof, comprising administering to the subject a pharmaceutical composition described herein.

In some embodiments of a method of treating a bacterial infection, the pharmaceutical composition is administered by intravenous (IV) infusion.

In some embodiments of a method of treating a bacterial infection, a period of infusion of the pharmaceutical composition is about 2 hours.

Also disclosed herein is a crystalline form of (R)-3-(2-(trans-4-(2-aminoethylamino)cyclohexyl)acetamido)-2-hydroxy-3,4-dihydro-2H-benzo[e][1,2]oxaborinine-8-carboxylic acid:

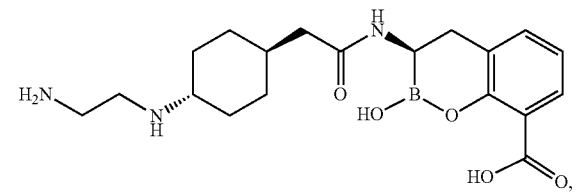 [SMILES: NCCN[C@H]1CC[C@H](CC(=O)N[C@H]2Cc3cccc(C(=O)O)c3OB2O)CC1]

a pharmaceutically acceptable salt, a solvate, or a pharmaceutically acceptable salt and solvate thereof.

Also disclosed herein is a crystalline form of (R)-3-(2-(trans-4-(2-aminoethylamino)cyclohexyl)acetamido)-2-hydroxy-3,4-dihydro-2H-benzo[e][1,2]oxaborinine-8-carboxylic acid:

dihydrochloride or a solvate thereof.

In some embodiments of a crystalline form, (R)-3-(2-(trans-4-(2-aminoethylamino)cyclohexyl)acetamido)-2-hydroxy-3,4-dihydro-2H-benzo[e][1,2]oxaborinine-8-carboxylic acid dihydrochloride is in the form of a monohydrate solvate.

In some embodiments of a crystalline form, the crystalline form has an X-Ray powder diffraction (XRPD) pattern substantially the same as shown in FIG. 2.

In some embodiments of a crystalline form, the crystalline form has an X-Ray powder diffraction (XRPD) pattern substantially the same as shown in FIG. 3.

In some embodiments of a crystalline form, the crystalline form has an X-ray powder diffraction (XRPD) pattern comprising characteristic peaks at about 7.0°±0.1° 2θ, about 14.1°±0.1° 2θ, about 20.2°±0.1° 2θ, about 24.6°±0.1° 2θ, and about 27.7°±0.1° 2θ.

In some embodiments of a crystalline form, the X-ray powder diffraction (XRPD) pattern further comprises characteristic peaks at about 10.5°±0.1° 2θ, about 18.9°±0.1° 2θ, about 23.7°±0.1° 2θ, about 25.6°±0.1° 2θ, and about 29.6°±0.1° 2θ.

In some embodiments of a crystalline form, (R)-3-(2-(trans-4-(2-aminoethylamino)cyclohexyl)acetamido)-2-hydroxy-3,4-dihydro-2H-benzo[e][1,2]oxaborinine-8-carboxylic acid dihydrochloride is anhydrous.

In some embodiments of a crystalline form, the crystalline form has an X-Ray powder diffraction (XRPD) pattern substantially the same as shown in FIG. 8.

In some embodiments of a crystalline form, the crystalline form has an X-ray powder diffraction (XRPD) pattern comprising characteristic peaks at about 7.3°±0.1° 2θ, about 14.5°±0.1° 2θ, about 18.0°±0.1° 2θ, about 19.7°±0.1° 2θ, about 24.0°±0.1° 2θ, and about 27.3°±0.1° 2θ.

In some embodiments of a crystalline form, the X-ray powder diffraction (XRPD) pattern further comprises characteristic peaks at about 10.8°±0.1° 2θ, about 16.6°±0.1° 2θ, about 19.6°±0.1° 2θ, about 23.3°±0.1° 2θ, about 24.3°±0.1° 2θ, and about 29.3°±0.1° 2θ.

Also disclosed herein is a pharmaceutical composition comprising:
  (i) a crystalline form disclosed herein, a pharmaceutically acceptable salt, a solvate, or a pharmaceutically acceptable salt and solvate thereof; and
  (ii) cefepime.

In some embodiments of a pharmaceutical composition, the pharmaceutical composition is formulated as a homogeneous liquid suitable for injection.

In some embodiments of a pharmaceutical composition, the pharmaceutical composition further comprises an aqueous carrier.

In some embodiments of a pharmaceutical composition, the pharmaceutical composition has a pH from about 4 to about 6.

In some embodiments of a pharmaceutical composition, the pharmaceutical composition is formulated as a powder for reconstitution.

In some embodiments of a pharmaceutical composition, the pharmaceutical composition is suitable for injection once reconstituted with an aqueous carrier.

In some embodiments of a pharmaceutical composition, the pharmaceutical composition further comprises a pharmaceutically acceptable excipient.

In some embodiments of a pharmaceutical composition, the pharmaceutically acceptable excipient is an amino acid or a monosaccharide derivative.

In some embodiments of a pharmaceutical composition, the pharmaceutically acceptable excipient is L-arginine.

In some embodiments of a pharmaceutical composition, the pharmaceutically acceptable excipient is meglumine.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1A:
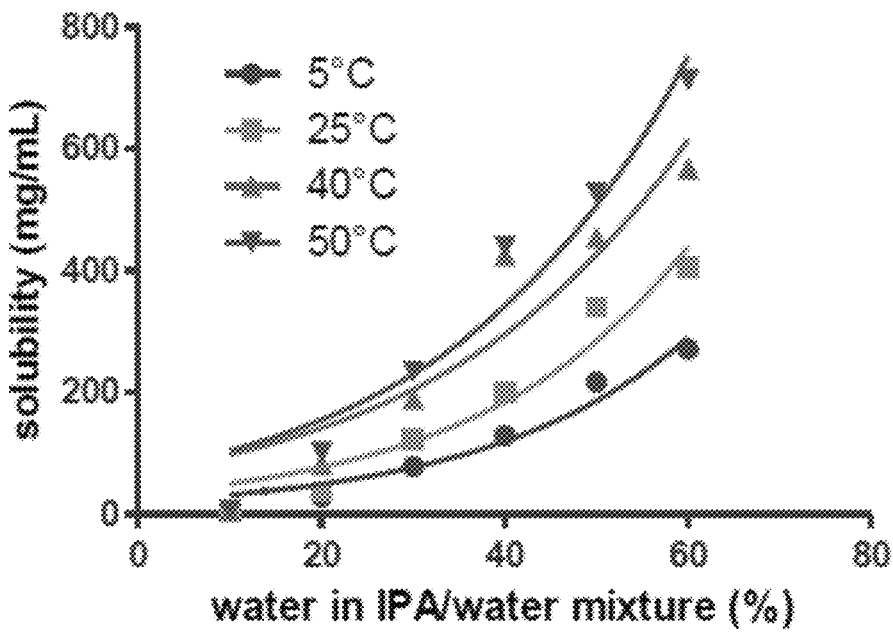
FIG. 1A shows the solubility values of Compound 1-dihydrochloride in IPA/water mixtures at 5, 25, 40, and 50° C. as a function of the IPA/water content.

Disclosed herein are crystalline forms of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

Also disclosed herein are pharmaceutical compositions comprising crystalline forms of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

Also disclosed herein are pharmaceutical compositions comprising solid forms of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

As used herein, (R)-3-(2-(trans-4-(2-aminoethylamino)cyclohexyl)acetamido)-2-hydroxy-3,4-dihydro-2H-benzo[e][1,2]oxaborinine-8-carboxylic acid is as shown in the structure below:

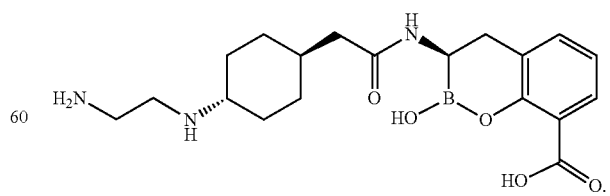

In some embodiments, (R)-3-(2-(trans-4-(2-aminoethylamino)cyclohexyl)acetamido)-2-hydroxy-3,4-dihydro-2H-benzo[e][1,2]oxaborinine-8-carboxylic acid is also referred to as Compound 1. In some embodiments, Compound 1 exists in an equilibrium between the "closed" cyclic form (as shown above) and the "open" acyclic form:

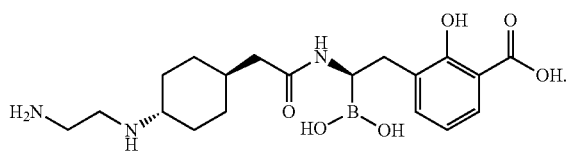 [SMILES: NCCN[C@H]1CC[C@H](CC(=O)N[C@@H](Cc2cccc(C(=O)O)c2O)B(O)O)CC1]

In some embodiments, Compound 1 associates into intramolecular dimers, trimers, and any combinations thereof. In some embodiments, Compound 1 is in the form of a pharmaceutically acceptable salt. In some embodiments, the pharmaceutically acceptable salt is a hydrochloride salt. In some embodiments, the pharmaceutically acceptable salt is a dihydrochloride salt. In some embodiments, Compound 1 is in the form of a pharmaceutically acceptable solvate. Solvates contain either stoichiometric or non-stoichiometric amounts of a solvent, and, in some embodiments, are formed during the process of crystallization with pharmaceutically acceptable solvents such as water or organic solvents. In some embodiments, the solvent is not covalently bound to Compound 1. In some embodiments, the solvent is covalently bound to Compound 1. Hydrates are formed when the solvent is water, or alcoholates are formed when the solvent is alcohol. In general, the solvated forms are considered equivalent to the unsolvated forms for the purposes of the compounds and methods provided herein. In some embodiments, the pharmaceutically acceptable solvate is a monohydrate solvate.

Crystalline Forms

Disclosed herein are crystalline forms of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof. In some embodiments, the crystalline form is Form 1. In some embodiments, the crystalline form is Form 2. In some embodiments, the crystalline form is Form 3. In some embodiments, the crystalline form is Form 4. In some embodiments, the crystalline form is Form 5. In some embodiments, the crystalline form is Form 6.

Form 1

Figure 2:
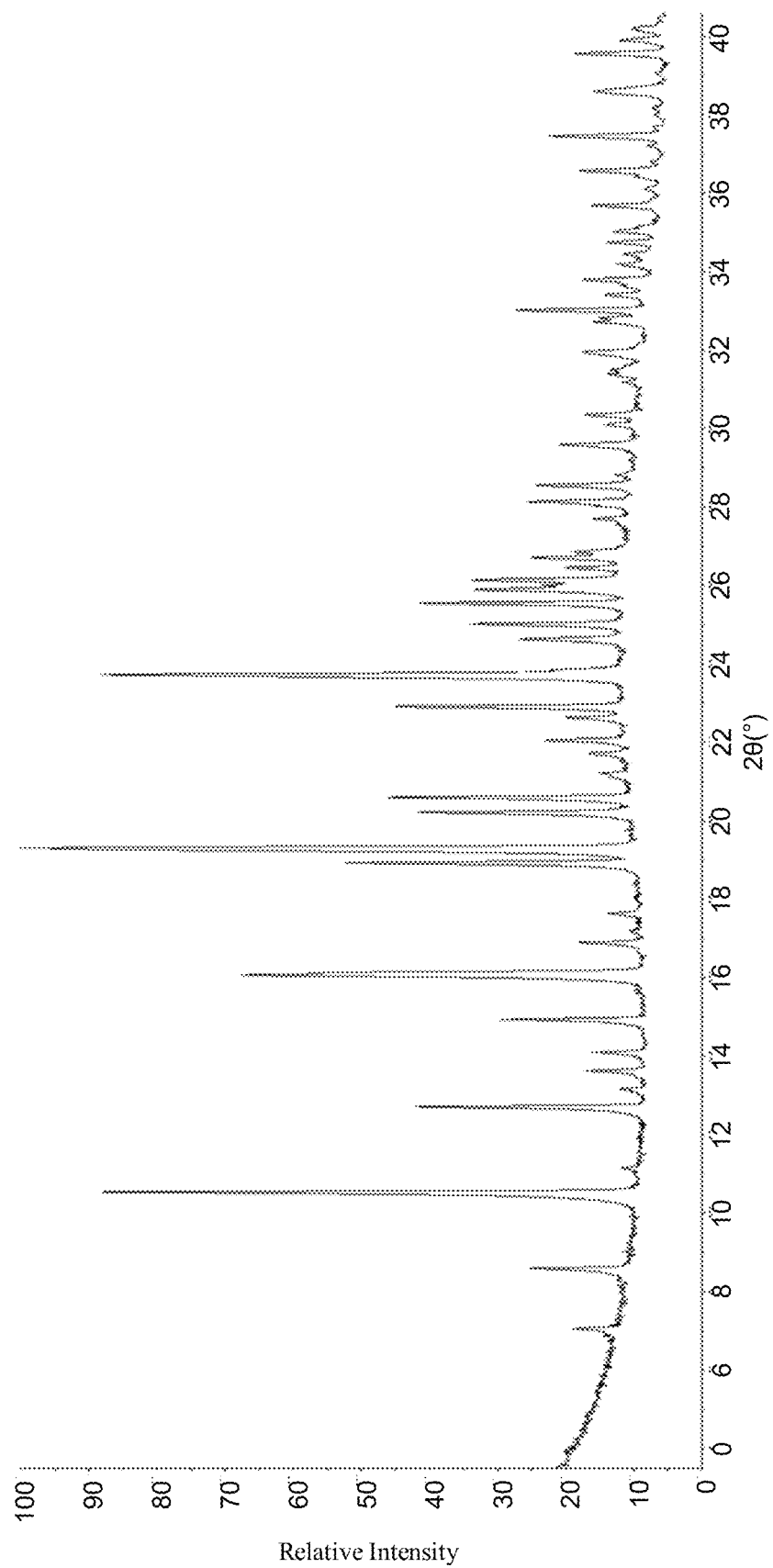
FIG. 2 shows the X-Ray Powder Diffraction pattern collected for Form 1 at room temperature.
Figure 3:
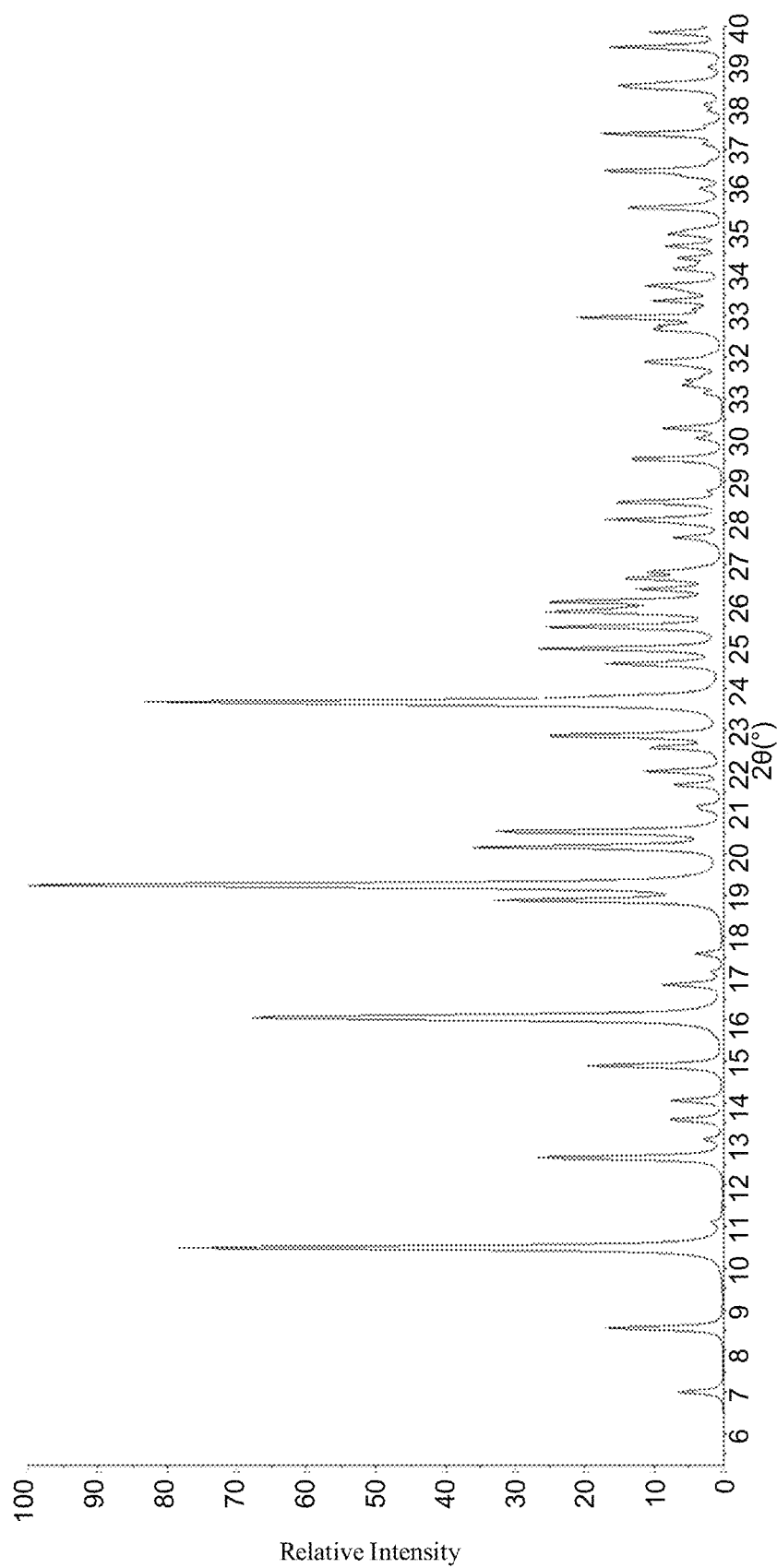
FIG. 3 shows the X-Ray Powder Diffraction pattern simulated from single crystal data for Form 1 collected at 100K.

In some embodiments, the dihydrochloride salt of Compound 1 is made into a pure and stable crystalline form (Form 1) under controlled conditions. In some embodiments, Form 1 is a monohydrate form of the dihydrochloride salt of Compound 1. In some embodiments, the X-ray powder diffraction (XRPD) pattern of Form 1 is substantially the same as shown in FIG. 2, with corresponding tabulated peak data shown in Table 1. In some embodiments, the X-ray powder diffraction (XRPD) pattern of Form 1 is substantially the same as shown in FIG. 3. The X-ray powder diffraction (XRPD) pattern shown in FIG. 2 is substantially the same as the X-ray powder diffraction (XRPD) pattern shown in FIG. 3.

TABLE 1

| 2 θ [°] | d value [Å] | Intensity [%] |
|---|---|---|
| 7.0 | 12.54 | 19 |
| 8.6 | 10.29 | 25 |
| 10.5 | 8.39 | 88 |

TABLE 1-continued

| 2 θ [°] | d value [Å] | Intensity [%] |
|---|---|---|
| 11.2 | 7.93 | 12 |
| 12.7 | 6.96 | 42 |
| 13.1 | 6.73 | 12 |
| 13.6 | 6.50 | 17 |
| 14.1 | 6.28 | 16 |
| 14.9 | 5.93 | 30 |
| 16.1 | 5.51 | 68 |
| 16.9 | 5.24 | 18 |
| 17.2 | 5.15 | 11 |
| 17.6 | 5.02 | 14 |
| 18.9 | 4.69 | 52 |
| 19.3 | 4.60 | 100 |
| 20.2 | 4.39 | 42 |
| 20.6 | 4.31 | 46 |
| 21.2 | 4.19 | 15 |
| 21.7 | 4.09 | 17 |
| 22.1 | 4.03 | 23 |
| 22.6 | 3.93 | 20 |
| 22.9 | 3.88 | 45 |
| 23.7 | 3.75 | 88 |
| 24.6 | 3.61 | 27 |
| 25.0 | 3.56 | 34 |
| 25.6 | 3.48 | 42 |
| 25.9 | 3.44 | 34 |
| 26.1 | 3.41 | 34 |
| 26.5 | 3.37 | 20 |
| 26.7 | 3.33 | 25 |
| 26.9 | 3.32 | 19 |
| 27.7 | 3.22 | 16 |
| 28.1 | 3.17 | 26 |
| 28.6 | 3.12 | 25 |
| 28.8 | 3.09 | 13 |
| 29.6 | 3.02 | 21 |
| 30.1 | 2.97 | 14 |
| 30.3 | 2.94 | 17 |
| 31.2 | 2.87 | 12 |
| 31.4 | 2.85 | 14 |
| 31.5 | 2.84 | 13 |
| 31.9 | 2.80 | 18 |
| 32.7 | 2.73 | 16 |
| 32.8 | 2.73 | 15 |
| 33.0 | 2.71 | 27 |
| 33.4 | 2.68 | 15 |
| 33.6 | 2.66 | 12 |
| 33.8 | 2.65 | 18 |
| 34.2 | 2.62 | 13 |
| 34.4 | 2.60 | 12 |
| 34.7 | 2.58 | 14 |
| 35.0 | 2.56 | 13 |
| 35.7 | 2.51 | 16 |
| 36.1 | 2.48 | 9 |
| 36.4 | 2.47 | 10 |
| 36.6 | 2.45 | 18 |
| 36.8 | 2.44 | 8 |
| 37.2 | 2.41 | 8 |
| 37.5 | 2.40 | 23 |
| 37.7 | 2.39 | 7 |
| 38.0 | 2.37 | 7 |
| 38.2 | 2.36 | 7 |
| 38.6 | 2.33 | 16 |
| 39.1 | 2.30 | 7 |
| 39.6 | 2.28 | 19 |
| 39.9 | 2.26 | 12 |

In some embodiments, Form 1 exhibits an X-ray powder diffraction pattern that includes at least three characteristic peaks selected from peaks at about 7.0°±0.1° 2θ, about 10.5°±0.1° 2θ, about 14.1°±0.1° 2θ, about 18.9°±0.1° 2θ, about 20.2°±0.1° 2θ, about 23.7°±0.1° 2θ, about 24.6°±0.1° 2θ, about 25.6°±0.1° 2θ, about 27.7°±0.1° 2θ, and about 29.6°±0.1° 2θ. In some embodiments, Form 1 exhibits an X-ray powder diffraction (XRPD) pattern that comprises characteristic peaks at about 7.0°±0.1° 2θ, about 14.1°±0.1° 2θ, about 20.2°±0.1° 2θ, about 24.6°±0.1° 2θ, and about 27.7°±0.1° 2θ. In some embodiments, Form 1 exhibits an X-ray powder diffraction (XRPD) pattern that further comprises characteristic peaks at about 10.5°±0.1° 2θ, about 18.9°±0.1° 2θ, about 23.7°±0.1° 2θ, about 25.6°±0.1° 2θ, and about 29.6°±0.1° 2θ. In some embodiments, Form 1 exhibits an X-ray powder diffraction (XRPD) pattern that comprises characteristic peaks at about 10.5°±0.1° 2θ, about 12.7°±0.1° 2θ, about 16.1°±0.1° 2θ, about 18.9°±0.1° 2θ, about 19.3°±0.1° 2θ, about 20.2°±0.1° 2θ, about 20.6°±0.1° 2θ, about 22.9°±0.1° 2θ, about 23.7°±0.1° 2θ, and about 25.6°±0.1° 2θ. In some embodiments, Form 1 exhibits an X-ray powder diffraction (XRPD) pattern that comprises characteristic peaks at about 10.5°±0.1° 2θ, about 12.7°±0.1° 2θ, about 14.9°±0.1° 2θ, about 16.1°±0.1° 2θ, about 18.9°±0.1° 2θ, about 19.3°±0.1° 2θ, about 20.2°±0.1° 2θ, about 20.6°±0.1° 2θ, about 22.9°±0.1° 2θ, about 23.7°±0.1° 2θ, about 25.0°±0.1° 2θ, about 25.6°±0.1° 2θ, about 25.9°±0.1° 2θ, and about 26.1°±0.1° 2θ. In some embodiments, Form 1 exhibits an X-ray powder diffraction (XRPD) pattern that comprises characteristic peaks at about 8.6°±0.1° 2θ, about 10.5°±0.1° 2θ, about 12.7°±0.1° 2θ, about 14.9°±0.1° 2θ, about 16.1°±0.1° 2θ, about 18.9°±0.1° 2θ, about 19.3°±0.1° 2θ, about 20.2X°±0.1° 2θ, about 20.6°±0.1° 2θ, about 22.1°±0.1° 2θ, about 22.6°±0.1° 2θ, about 22.9°±0.1° 2θ, about 23.7°±0.1° 2θ, about 24.6°±0.1° 2θ, about 25.0°±0.1° 2θ, about 25.6°±0.1° 2θ, about 25.9°±0.1° 2θ, about 26.1°±0.1° 2θ, about 26.5°±0.1° 2θ, about 26.7°±0.1° 2θ, about 28.1°±0.1° 2θ, about 28.6°±0.1° 2θ, about 29.6°±0.1° 2θ, about 33.0°±0.1° 2θ, and about 37.5°±0.1° 2θ.

Form 2

Figure 8:
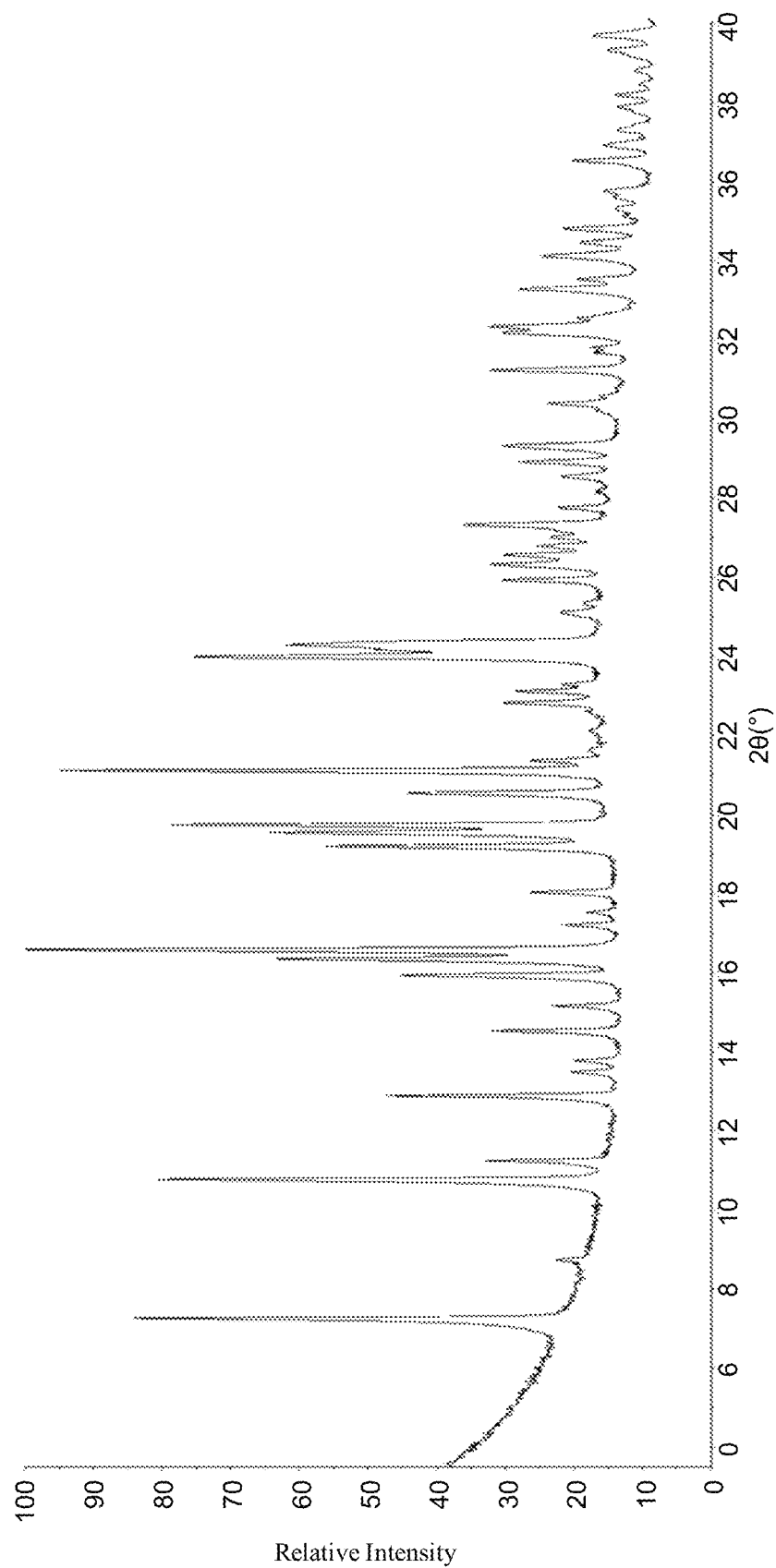
FIG. 8 shows the X-Ray Powder Diffraction pattern collected for Form 2 at room temperature.

In some embodiments, the dihydrochloride salt of Compound 1 can be made into a pure and stable crystalline form (Form 2) under controlled conditions. In some embodiments, Form 2 is an anhydrous form of the dihydrochloride salt of Compound 1. The X-ray powder diffraction (XRPD) pattern of Form 2 is substantially the same as shown in FIG. 8, with corresponding tabulated peak data shown in Table 2.

TABLE 2

| 2 θ [°] | d value [Å] | Intensity [%] |
|---|---|---|
| 7.3 | 12.17 | 84 |
| 8.7 | 10.11 | 23 |
| 10.8 | 8.21 | 81 |
| 11.2 | 7.86 | 33 |
| 12.9 | 6.87 | 47 |
| 13.5 | 6.56 | 20 |
| 13.8 | 6.42 | 20 |
| 14.5 | 6.09 | 32 |
| 15.2 | 5.84 | 23 |
| 15.9 | 5.56 | 45 |
| 16.3 | 5.42 | 63 |
| 16.6 | 5.34 | 100 |
| 17.2 | 5.15 | 22 |
| 17.5 | 5.06 | 18 |
| 18.0 | 4.91 | 26 |
| 19.2 | 4.62 | 56 |
| 19.6 | 4.54 | 64 |
| 19.7 | 4.50 | 79 |
| 20.5 | 4.32 | 44 |
| 21.1 | 4.20 | 95 |
| 21.4 | 4.15 | 26 |
| 21.6 | 4.11 | 18 |
| 22.1 | 4.01 | 18 |
| 22.8 | 3.89 | 30 |
| 23.1 | 3.84 | 29 |
| 23.3 | 3.82 | 22 |
| 24.0 | 3.71 | 75 |
| 24.3 | 3.66 | 62 |
| 25.1 | 3.54 | 22 |
| 25.3 | 3.51 | 19 |
| 25.9 | 3.43 | 31 |
| 26.3 | 3.38 | 32 |
| 26.6 | 3.35 | 30 |
| 26.8 | 3.32 | 26 |
| 27.0 | 3.30 | 24 |
| 27.3 | 3.26 | 36 |
| 27.8 | 3.21 | 22 |
| 28.2 | 3.16 | 17 |
| 28.6 | 3.12 | 22 |
| 28.9 | 3.09 | 28 |
| 29.3 | 3.04 | 31 |
| 30.2 | 2.96 | 17 |
| 30.4 | 2.94 | 24 |
| 30.6 | 2.92 | 16 |
| 31.2 | 2.86 | 32 |
| 31.7 | 2.82 | 17 |
| 31.8 | 2.81 | 18 |
| 32.2 | 2.78 | 31 |
| 32.3 | 2.77 | 32 |
| 32.6 | 2.75 | 20 |
| 33.3 | 2.69 | 28 |
| 33.5 | 2.67 | 20 |
| 34.1 | 2.63 | 25 |
| 34.5 | 2.60 | 19 |
| 34.8 | 2.57 | 22 |
| 35.1 | 2.55 | 13 |
| 35.3 | 2.54 | 14 |
| 35.6 | 2.52 | 14 |
| 35.8 | 2.51 | 16 |
| 36.5 | 2.46 | 21 |
| 36.9 | 2.43 | 16 |
| 37.3 | 2.41 | 14 |
| 37.9 | 2.37 | 14 |
| 38.2 | 2.35 | 14 |
| 38.5 | 2.34 | 11 |
| 38.8 | 2.32 | 11 |
| 39.2 | 2.30 | 12 |
| 39.3 | 2.29 | 15 |
| 39.7 | 2.27 | 17 |
| 40.2 | 2.24 | 10 |
| 40.6 | 2.22 | 11 |
| 40.8 | 2.21 | 10 |
| 41.3 | 2.18 | 11 |

In some embodiments, Form 2 exhibits an X-ray powder diffraction pattern that includes at least three characteristic peaks selected from peaks at about 7.3°±0.1° 2θ, about 10.8°±0.1° 2θ, about 14.5°±0.1° 2θ, about 16.6°±0.1° 2θ, about 18.0°±0.1° 2θ, at about 19.6°±0.1° 2θ, about 19.7°±0.1° 2θ, about 23.3°±0.1° 2θ, about 24.0°±0.1° 2θ, about 24.3°±0.1° 2θ, about 27.3°±0.1° 2θ, and about 29.3°±0.1° 2θ. In some embodiments, Form 2 exhibits an X-ray powder diffraction (XRPD) pattern that comprises characteristic peaks at about 7.3°±0.1° 2θ, about 14.5°±0.1° 2θ, about 18.0°±0.1° 2θ, about 19.7°±0.1° 2θ, about 24.0°±0.1° 2θ, and about 27.3°±0.1° 2θ. In some embodiments, Form 2 exhibits an X-ray powder diffraction (XRPD) pattern that further comprises characteristic peaks at about 10.8°±0.1° 2θ, about 16.6°±0.1° 2θ, about 19.6°±0.1° 2θ, about 23.3°±0.1° 2θ, about 24.3°±0.1° 2θ, and about 29.3°±0.1° 2θ. In some embodiments, Form 2 exhibits an X-ray powder diffraction (XRPD) pattern that comprises characteristic peaks at about 7.3°±0.1° 2θ, about 10.8°±0.1° 2θ, about 12.9°±0.1° 2θ, about 15.9°±0.1° 2θ, about 16.3°±0.1° 2θ, about 16.6°±0.1° 2θ, about 19.2°±0.1° 2θ, about 19.7°±0.1° 2θ, about 20.5°±0.1° 2θ, about 21.1°±0.1° 2θ, about 24.0°±0.1° 2θ, and about 24.3°±0.1° 2θ. In some embodiments, Form 2 exhibits an X-ray powder diffraction (XRPD) pattern that comprises characteristic peaks at about 7.3°±0.1° 2θ, about 10.8°±0.1° 2θ, about 11.2°±0.1° 2θ, about 12.9°±0.1° 2θ, about 14.5°±0.1° 2θ, about 15.9°±0.1° 2θ, about 16.3°±0.1° 2θ, about 16.6°±0.1° 2θ, about 19.2°±0.1° 2θ, about 19.7°±0.1° 2θ, about 20.5°±0.1° 2θ, about 21.1°±0.1° 2θ, about 22.8°±0.1° 2θ, about 24.0°±0.1° 2θ, about 24.3°±0.1° 2θ, about 25.9°±0.1° 2θ, about 26.3°±0.1° 2θ, about 26.6°±0.1° 2θ, about 29.3°±0.1° 2θ, and about 32.3°±0.1° 2θ.

Form 3

Figure 12:
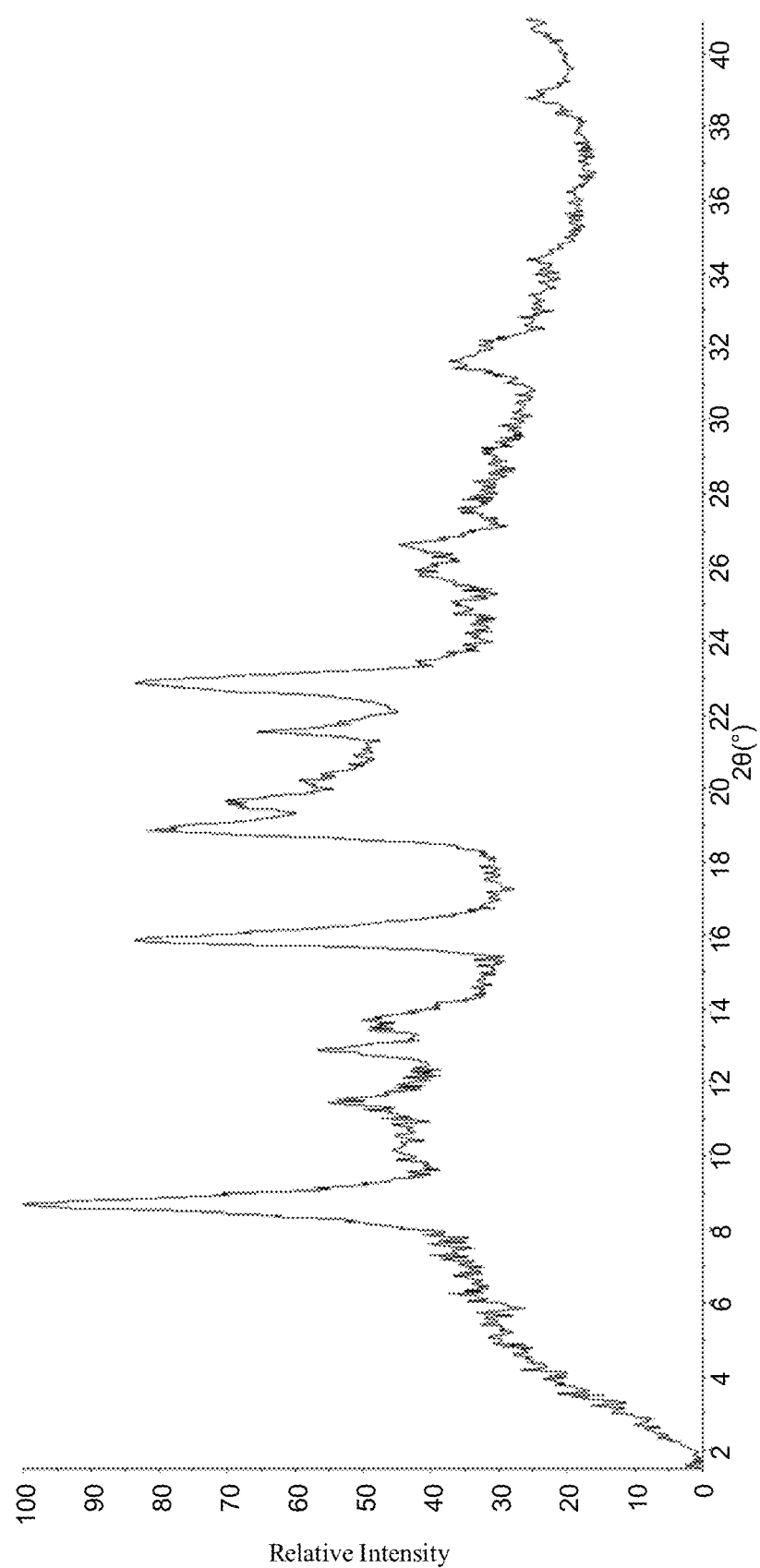
FIG. 12 shows the X-Ray Powder Diffraction pattern collected for Form 3.

In some embodiments, the dihydrochloride salt of Compound 1 can be made into a new form (Form 3) under controlled conditions. The X-ray powder diffraction (XRPD) pattern of Form 3 is substantially the same as shown in FIG. 12, with corresponding tabulated peak data shown in Table 3.

TABLE 3

| 2 θ [°] | d value [Å] | Intensity [%] |
|---|---|---|
| 8.68 | 10.18 | 100 |
| 15.92 | 5.56 | 82.5 |
| 18.91 | 4.69 | 81.8 |
| 21.58 | 4.11 | 65.7 |
| 22.86 | 3.89 | 83.7 |

Form 4

Figure 13:
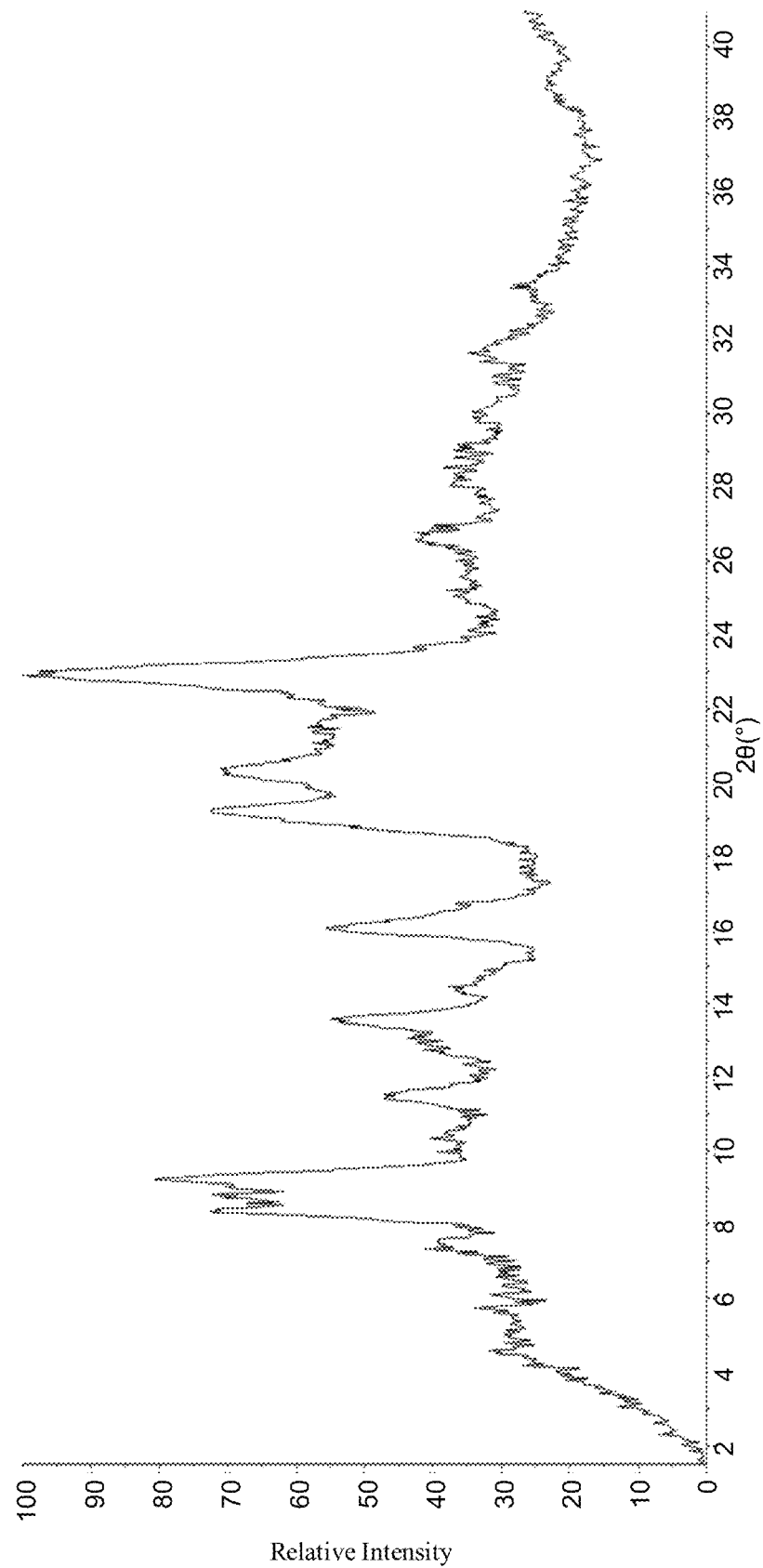
FIG. 13 shows the X-Ray Powder Diffraction pattern collected for Form 4.

In some embodiments, the dihydrochloride salt of Compound 1 can be made into a new form (Form 4) under controlled conditions. The X-ray powder diffraction (XRPD) pattern of Form 4 is substantially the same as shown in FIG. 13, with corresponding tabulated peak data shown in Table 4.

TABLE 4

| 2 θ [°] | d value [Å] | Intensity [%] |
|---|---|---|
| 8.34 | 10.58 | 72.7 |
| 8.75 | 10.11 | 71.0 |
| 8.82 | 10.01 | 72.0 |
| 9.22 | 9.58 | 80.9 |
| 18.94 | 4.68 | 62.2 |
| 20.38 | 4.35 | 72.0 |
| 22.90 | 3.88 | 100 |

Form 5

Figure 14:
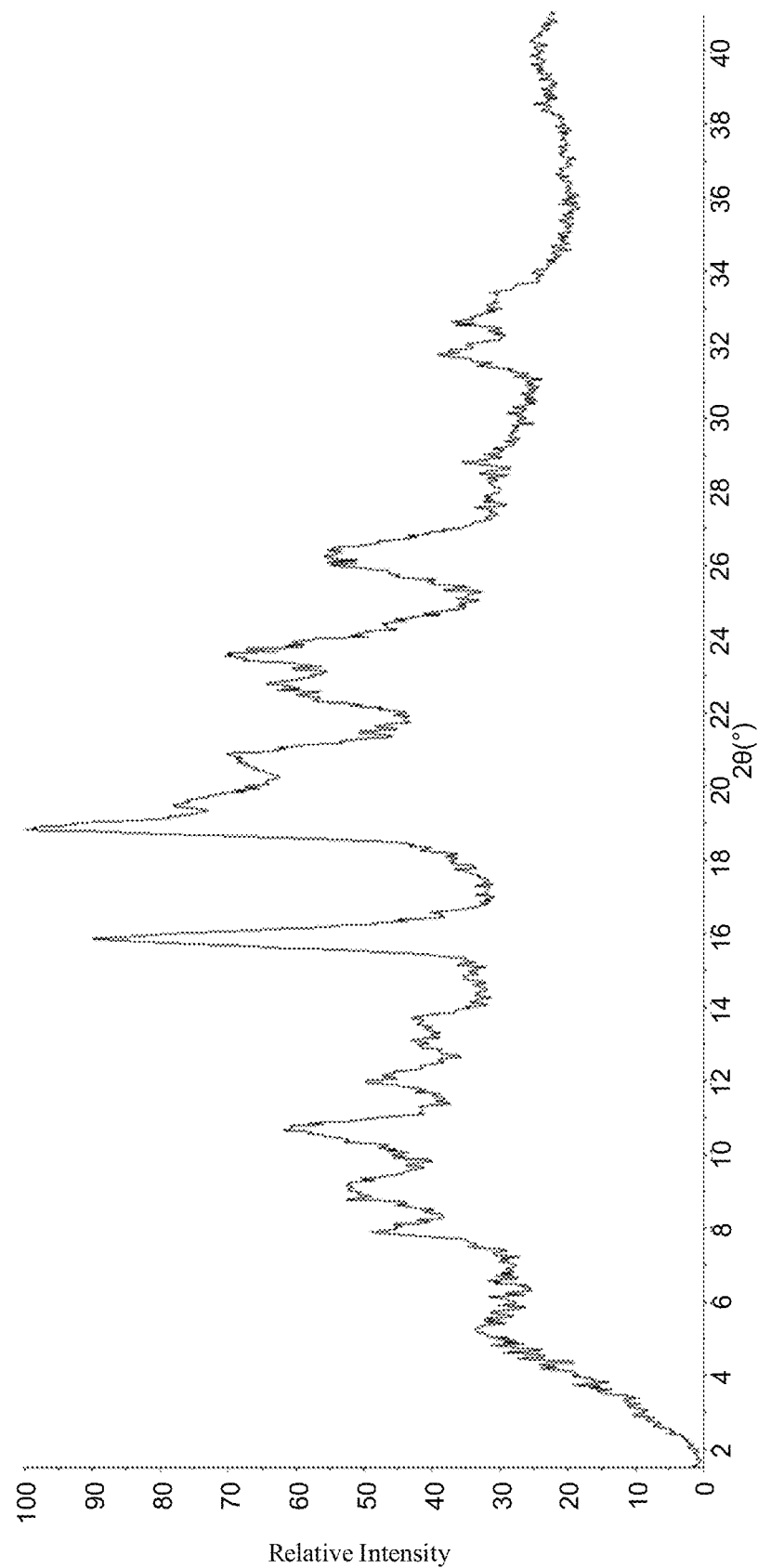
FIG. 14 shows the X-Ray Powder Diffraction pattern collected for Form 5.

In some embodiments, the dihydrochloride salt of Compound 1 can be made into a new form (Form 5) under controlled conditions. The X-ray powder diffraction (XRPD) pattern of Form 5 is substantially the same as shown in FIG. 14, with corresponding tabulated peak data shown in Table 5.

TABLE 5

| 2 θ [°] | d value [Å] | Intensity [%] |
|---|---|---|
| 7.90 | 11.18 | 47.3 |
| 10.65 | 8.29 | 62.9 |
| 15.86 | 5.57 | 91.2 |
| 18.82 | 4.71 | 100 |

Form 6

Figure 15:
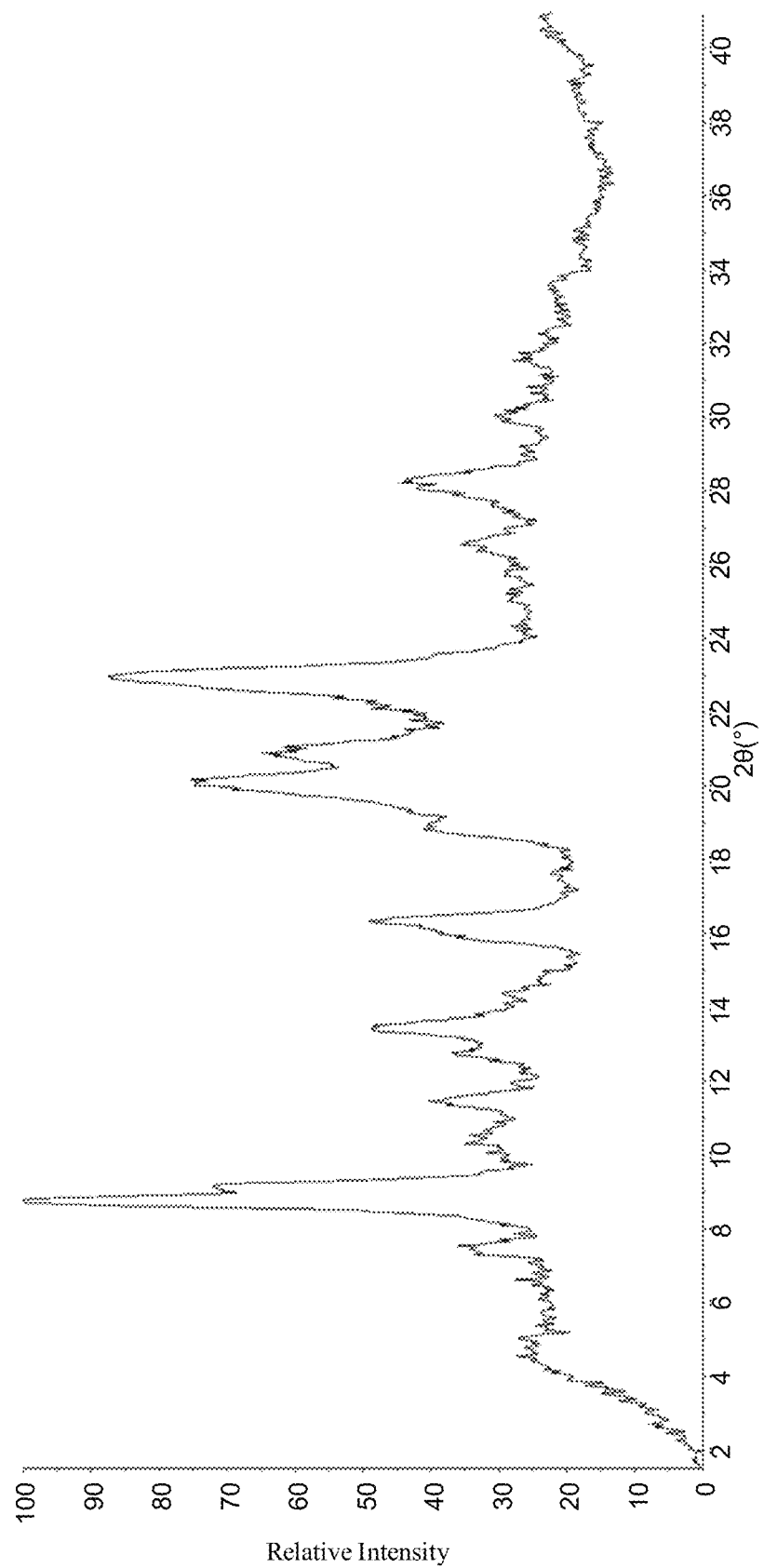
FIG. 15 shows the X-Ray Powder Diffraction pattern collected for Form 6.

In some embodiments, the dihydrochloride salt of Compound 1 can be made into a crystalline form (Form 6) under controlled conditions. The X-ray powder diffraction (XRPD) pattern of Form 6 is substantially the same as shown in FIG. 15, with corresponding tabulated peak data shown in Table 6.

TABLE 6

| 2 θ [°] | d value [Å] | Intensity [%] |
|---|---|---|
| 8.74 | 10.11 | 100 |
| 8.81 | 10.02 | 72.2 |
| 13.38 | 6.61 | 48.8 |
| 16.30 | 5.43 | 49.1 |
| 20.06 | 4.42 | 77.6 |
| 22.86 | 3.89 | 87.7 |
| 28.30 | 3.15 | 44.7 |

EMBODIMENTS

Embodiment P1: A crystalline form of (R)-3-(2-(trans-4-(2-aminoethylamino)cyclohexyl)acetamido)-2-hydroxy-3,4-dihydro-2H-benzo[e][1,2]oxaborinine-8-carboxylic acid:

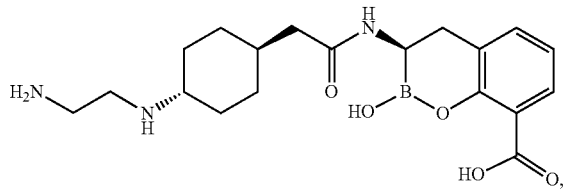 [SMILES: NCCN[C@H]1CC[C@H](CC(=O)N[C@H]2Cc3cccc(C(=O)O)c3OB2O)CC1]

a pharmaceutically acceptable salt, and/or a solvate thereof.

Embodiment P2: A crystalline form of (R)-3-(2-(trans-4-(2-aminoethylamino)cyclohexyl)acetamido)-2-hydroxy-3,4-dihydro-2H-benzo[e][1,2]oxaborinine-8-carboxylic acid:

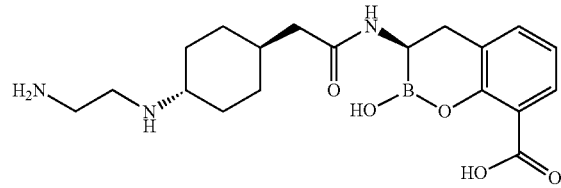 [SMILES: NCCN[C@H]1CC[C@H](CC(=O)N[C@H]2Cc3cccc(C(=O)O)c3OB2O)CC1]

dihydrochloride, and/or a solvate thereof.

Embodiment P3: The crystalline form of Embodiment P2, wherein (R)-3-(2-(trans-4-(2-aminoethylamino)cyclohexyl) acetamido)-2-hydroxy-3,4-dihydro-2H-benzo[e][1,2]oxaborinine-8-carboxylic acid dihydrochloride is in the form of a monohydrate solvate.

Embodiment P4: The crystalline form of Embodiment P3, wherein the crystalline form has at least one of the following properties:
  (a) an X-Ray powder diffraction (XRPD) pattern substantially the same as shown in FIG. 2; or
  (b) an X-Ray powder diffraction (XRPD) pattern substantially the same as shown in FIG. 3; or
  (c) an X-ray powder diffraction (XRPD) pattern comprising characteristic peaks at about 7.0°±0.1° 2θ, about 14.1°±0.1° 2θ, about 20.2°±0.1° 2θ, about 24.6°±0.1° 2θ, and about 27.7°±0.1° 2θ.

Embodiment P5: The crystalline form of Embodiment P4, wherein the X-ray powder diffraction (XRPD) pattern further comprises characteristic peaks at about 10.5°±0.1° 2θ, about 18.9°±0.1° 2θ, about 23.7°±0.1° 2θ, about 25.6°±0.1° 2θ, and about 29.6°±0.1° 2θ.

Embodiment P6: The crystalline form of any one of Embodiment P3-P5, wherein the crystalline form is Form 1.

Embodiment P7: The crystalline form of Embodiment P2, wherein (R)-3-(2-(trans-4-(2-aminoethylamino)cyclohexyl)

acetamido)-2-hydroxy-3,4-dihydro-2H-benzo[e][1,2]oxaborinine-8-carboxylic acid dihydrochloride is anhydrous.

Embodiment P8: The crystalline form of Embodiment P7, wherein the crystalline form has at least one of the following properties:
(a) an X-Ray powder diffraction (XRPD) pattern substantially the same as shown in FIG. 8; or
(b) an X-ray powder diffraction (XRPD) pattern comprising characteristic peaks at about 7.3°±0.1° 2θ, about 14.5°±0.1° 2θ, about 18.0°±0.1° 2θ, about 19.7°±0.1° 2θ, about 24.0°±0.1° 2θ, and about 27.3°±0.1° 2θ.

Embodiment P9: The crystalline form of Embodiment P8, wherein the X-ray powder diffraction (XRPD) pattern further comprises characteristic peaks at about 10.8°±0.1° 2θ, about 16.6°±0.1° 2θ, about 19.6°±0.1° 2θ, about 23.3°±0.1° 2θ, about 24.3°±0.1° 2θ, and about 29.3°±0.1° 2θ.

Embodiment P10: The crystalline form of any one of Embodiment P7-P9, wherein the crystalline form is Form 2.

Pharmaceutical Compositions

Disclosed herein is a pharmaceutical composition comprising:
(i) (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof; and
(ii) cefepime.

In some embodiments, (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is amorphous. In some embodiments, (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is crystalline.

Also disclosed herein is a pharmaceutical composition comprising:
(i) crystalline (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof; and
(ii) cefepime.

In some embodiments of the pharmaceutical composition, (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is in the form of a crystalline form disclosed herein. In some embodiments, the crystalline form of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is Form 1. In some embodiments, the crystalline form of (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is Form 2.

In some embodiments, the pharmaceutical compositions described herein are provided in unit dosage form. As used herein, a "unit dosage form" is a composition containing an amount of compound 1 that is suitable for administration to an animal, preferably mammal, subject in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. In some embodiments, Compound 1 and cefepime are formulated in separate containers. In some embodiments, Compound 1 and cefepime are formulated in a single container.

In some embodiments, administration of Compound 1, a pharmaceutically acceptable salt, a solvate, or a pharmaceutically acceptable salt and solvate thereof is via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. In some embodiments, the administration is oral administration. In some embodiments, the administration is intravenous administration. In some embodiments, the administration is intramuscular administration.

Standard pharmaceutical formulation techniques are used, such as those disclosed in Remington's The Science and Practice of Pharmacy, 21st Ed., Lippincott Williams & Wilkins (2005), incorporated by reference for such disclosures.

In some embodiments, the pharmaceutical composition comprises a pharmaceutically acceptable excipient. The term "pharmaceutically acceptable excipient", as used herein, means one or more compatible solid or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. In some embodiments, the pharmaceutically acceptable excipient is of sufficiently high purity and sufficiently low toxicity to render them suitable for administration preferably to an animal, preferably mammal, being treated.

Some examples of substances, which can serve as pharmaceutically acceptable excipients include:
Amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, the amino acid is arginine. In some embodiments, the amino acid is L-arginine.
Monosaccharides such as glucose (dextrose), arabinose, mannitol, fructose (levulose), and galactose.
Monosaccharide derivatives such as monosaccharide wherein one or more —OH groups has been replaced. In some embodiments of a monosaccharide derivative, one or more —OH groups on the monosaccharide has been replaced by one or more —NH$_2$ or —NH—CH$_3$ groups. In some embodiments, the monosaccharide derivative is meglumine. Other examples of a monosaccharide derivative include amino alcohols.

Cellulose and its derivatives such as sodium carboxymethyl cellulose, ethyl cellulose, and methyl cellulose.

Solid lubricants such as talc, stearic acid, and magnesium stearate.

Polyols such as propylene glycol, glycerin, sorbitol, mannitol, and polyethylene glycol.

Emulsifiers such as the polysorbates.

Wetting agents such sodium lauryl sulfate.

Diluents such as calcium carbonate, sodium carbonate, mannitol, and lactose.

Binders such as starches (corn starch and potato starch), gelatin, and sucrose.

Disintegrants such as starch, alginic acid, and croscarmelose.

Glidants such as silicon dioxide.

Coloring agents such as the FD&C dyes.

Sweeteners and flavoring agents, such as aspartame, saccharin, menthol, peppermint, and fruit flavors.

Preservatives such as benzalkonium chloride, PHMB, chlorobutanol, thimerosal, phenylmercuric acetate, phenylmercuric nitrate, parabens, and sodium benzoate.

Tonicity adjustors such as sodium chloride, potassium chloride, mannitol, and glycerin.

Antioxidants such as sodium bisulfite, acetone sodium bisulfite, sodium formaldehyde, sulfoxylate, thiourea, and EDTA.

pH adjuster such as NaOH, sodium carbonate, sodium acetate, HCl, and citric acid.

Cryoprotectants such as sodium or potassium phosphates, citric acid, tartaric acid, gelatin, and carbohydrates such as dextrose, mannitol, and dextran.

In some embodiments of a pharmaceutical composition, the pharmaceutical composition is formulated as a homogeneous liquid suitable for injection. In some embodiments, the pharmaceutical composition is formulated for intravenous/intramuscular administration.

In some embodiments of a pharmaceutical composition, the composition further comprises a pharmaceutically acceptable excipient. In some embodiments of a pharmaceutical composition, the pharmaceutically acceptable excipient is an amino acid, a monosaccharide, or a monosaccharide derivative. In some embodiments of a pharmaceutical composition, the pharmaceutically acceptable excipient is an amino acid or a monosaccharide derivative. In some embodiments of a pharmaceutical composition, the pharmaceutically acceptable excipient is an amino acid. In some embodiments of a pharmaceutical composition, the pharmaceutically acceptable excipient is arginine. In some embodiments of a pharmaceutical composition, the pharmaceutically acceptable excipient is L-arginine. In some embodiments of a pharmaceutical composition, the pharmaceutically acceptable excipient is a monosaccharide or a monosaccharide derivative. In some embodiments of a pharmaceutical composition, the pharmaceutically acceptable excipient is a monosaccharide derivative. In some embodiments of a pharmaceutical composition, the pharmaceutically acceptable excipient is meglumine.

Liquid Composition

In some embodiments, the pharmaceutical composition for intravenous/intramuscular administration is formulated as a homogeneous liquid suitable for injection. In some embodiments, the pharmaceutical composition further comprises an aqueous carrier. In some embodiments, the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof. In some embodiments, the aqueous carrier is water for injection. In some embodiments, the aqueous carrier is 0.9% sodium chloride injection.

pH of the Liquid Composition

In some embodiments, the pH of the homogeneous liquid is from about 4 to about 9. In some embodiments, the pH of the homogeneous liquid is about 4, about 4.4, about 5, about 5.5, about 6, about 6.5, about 7, about 7.5, about 8, about 8.5, or about 9. In some embodiments, the pH of the homogeneous liquid is from about 4 to about 6.

Powder for Reconstitution

In some embodiments, the pharmaceutical composition for intravenous/intramuscular administration is formulated as a powder for reconstitution. In some embodiments, the pharmaceutical composition is suitable for injection once reconstituted with an aqueous carrier.

In some embodiments, the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof.

Stability of the Powder for Reconstitution

The pharmaceutical compositions described herein are stable in various storage conditions including refrigerated, ambient, and accelerated conditions. In some embodiments, refrigerated condition is about 2° C., about 2.1° C., about 2.2° C., about 2.3° C., about 2.4° C., about 2.5° C., about 2.6° C., about 2.7° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., or about 8° C. Accelerated conditions include temperature and/or relative humidity (RH) that are at or above ambient levels (e.g. 25° C.±2° C./60% RH±5% RH). In some instances, an accelerated condition is at about 30° C., about 35° C., about 40° C., about 45° C., about 50° C., about 55° C., or about 60° C. In other instances, an accelerated condition is above 55% RH, about 65% RH, about 70% RH, about 75% RH, or about 80% RH. In further instances, an accelerated condition is about 40° C. or 60° C. at ambient humidity. In yet further instances, an accelerated condition is about 40° C.±2° C./75% RH±5% RH. In yet further instances, an accelerated condition is about 30° C.±2° C./65% RH±5% RH.

In some embodiments, the pharmaceutical composition is stable at about 5° C.±3° C. for at least 12 months. In some embodiments, the pharmaceutical composition is stable at about 25° C.±2° C./60% RH±5% RH for at least 12 months. In some embodiments, the pharmaceutical composition is stable at about 30° C.±2° C./65% RH±5% RH for at least 6 months. In some embodiments, the pharmaceutical composition is stable at about 40° C.±2° C./75% RH±5% RH for at least 6 months.

EMBODIMENTS

Embodiment P'1: A pharmaceutical composition comprising:
(i) (R)-3-(2-(trans-4-(2-aminoethylamino)cyclohexyl)acetamido)-2-hydroxy-3,4-dihydro-2H-benzo[e][1,2]oxaborinine-8-carboxylic acid:

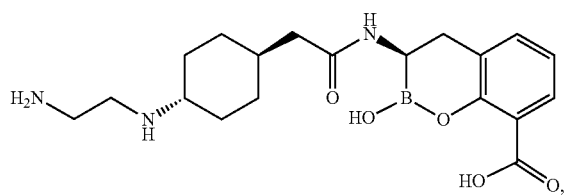 [SMILES: NCCN[C@H]1CC[C@H](CC(=O)N[C@H]2Cc3cccc(C(=O)O)c3OB2O)CC1]

a pharmaceutically acceptable salt, and/or a solvate thereof; and
(ii) cefepime.

Embodiment P'2: The pharmaceutical composition of Embodiment P'1, wherein the pharmaceutical composition is formulated as a homogeneous liquid suitable for injection.

Embodiment P'3: The pharmaceutical composition of Embodiment P'1 or P'2, further comprising a pharmaceutically acceptable excipient.

Embodiment P'4: The pharmaceutical composition of Embodiment P'3, wherein the pharmaceutically acceptable excipient is selected from amino acids.

Embodiment P'5: The pharmaceutical composition of Embodiment P'4, wherein the amino acid is L-arginine.

Embodiment P'6: The pharmaceutical composition of any one of Embodiment P'1-P'5, further comprising an aqueous carrier.

Embodiment P'7: The pharmaceutical composition of Embodiment P'6, wherein the aqueous carrier is selected from water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, and any combinations thereof.

Embodiment P'8: The pharmaceutical composition of any one of Embodiment P'2-P'7 having a pH from about 4 to about 9.

Embodiment P'9: The pharmaceutical composition of any one of Embodiment P'2-P'8 having a pH from about 4 to about 6.

Embodiment P'10: The pharmaceutical composition of Embodiment P'1, wherein the pharmaceutical composition is formulated as a powder for reconstitution.

Embodiment P'11: The pharmaceutical composition of Embodiment P'10, further comprising a pharmaceutically acceptable excipient.

Embodiment P'12: The pharmaceutical composition of Embodiment P'11, wherein the pharmaceutically acceptable excipient is selected from amino acids.

Embodiment P'13: The pharmaceutical composition of Embodiment P'12, wherein the amino acid is L-arginine.

Embodiment P'14: The pharmaceutical composition of any one of Embodiment P'10-P'13, wherein the pharmaceutical composition is suitable for injection once reconstituted with an aqueous carrier.

Embodiment P'15: The pharmaceutical composition of Embodiment P'14, wherein the aqueous carrier is selected from water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, and any combinations thereof.

Embodiment P'16: The pharmaceutical composition of any one of Embodiment P'10-P'15, wherein the pharmaceutical composition is stable at about 5° C.±3° C. for at least 12 months.

Embodiment P'17: The pharmaceutical composition of any one of Embodiment P'10-P'15, wherein the pharmaceutical composition is stable at about 25° C.±2° C./60% RH±5% RH for at least 12 months.

Embodiment P'18: The pharmaceutical composition of any one of Embodiment P'10-P'15, wherein the pharmaceutical composition is stable at about 30° C.±2° C./65% RH±5% RH for at least 6 months.

Embodiment P'19: The pharmaceutical composition of any one of Embodiment P'10-P'15, wherein the pharmaceutical composition is stable at about 40° C.±2° C./75% RH±5% RH for at least 6 months.

Embodiment P'20: A method of administering to a subject in need thereof, a pharmaceutical composition comprising:
(i) (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, and/or a solvate thereof; and
(ii) cefepime.

Embodiment P'21: The method of Embodiment P'20, wherein the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, and/or a solvate thereof, and the cefepime are formulated in separate containers.

Embodiment P'22: The method of Embodiment P'20 or P'21, wherein the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, and/or a solvate thereof is formulated in a first container.

Embodiment P'23: The method of any one of Embodiment P'20-P'22, wherein the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, and/or a solvate thereof is in the form of a first powder for reconstitution.

Embodiment P'24: The method of any one of Embodiment P'20-P'23, wherein the cefepime is formulated in a second container.

Embodiment P'25: The method of any one of Embodiment P'20-P'24, wherein the cefepime is in the form of a second powder for reconstitution.

Embodiment P'26: The method of Embodiment P'23 or P'25, the method comprising:
(a) mixing the first powder for reconstitution and the second powder for reconstitution to obtain a third powder for reconstitution;

(b) reconstituting the third powder for reconstitution of step (a) with an aqueous carrier to obtain a homogeneous liquid; and
(c) administering the homogeneous liquid of step (b) to the subject in need thereof.

Embodiment P'27: The method of Embodiment P'23 or P'25, the method comprising:
(a) reconstituting the first powder for reconstitution with a first aqueous carrier to obtain a first homogeneous liquid;
(b) reconstituting the second powder for reconstitution with a second aqueous carrier to obtain a second homogeneous liquid;
(c) mixing the first homogeneous liquid of step (a) and the second homogeneous liquid of step (b) to obtain a third homogeneous liquid; and
(d) administering the third homogeneous liquid of step (c) to the subject in need thereof.

Embodiment P'28: The method of Embodiment P'26 or P'27, wherein each of the aqueous carriers is independently selected from water for injection, 0.9% sodium chloride for injection, 5% dextrose for injection, 10% dextrose for injection, sodium lactate for injection, 5% dextrose and 0.9% sodium chloride for injection, lactated Ringers and 5% dextrose for injection, sodium chloride/sodium acetate/sodium gluconate/potassium chloride/magnesium chloride for injection, sodium chloride/potassium acetate/magnesium acetate in 5% dextrose for injection, and any combinations thereof.

Embodiment P'29: The method of Embodiment P'20, wherein the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, and/or a solvate thereof, and the cefepime are formulated in a single container.

Embodiment P'30: The method of Embodiment P'29, wherein the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, and/or a solvate thereof and the cefepime are in the form of a powder for reconstitution.

Embodiment P'31: The method of Embodiment P'30, the method comprising:
(a) reconstituting the powder for reconstitution with an aqueous carrier to obtain a homogeneous liquid; and
(b) administering the homogeneous liquid of step (a) to the subject in need thereof.

Embodiment P'32: The method of Embodiment P'31, wherein the aqueous carrier is selected from water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, and any combinations thereof.

Embodiment P'33: The method of any one of Embodiment P'20-P'32, wherein the pharmaceutical composition further comprises a pharmaceutically acceptable excipient.

Embodiment P'34: The method of Embodiment P'33, wherein the pharmaceutically acceptable excipient is selected from amino acids.

Embodiment P'35: The method of Embodiment P'34, wherein the pharmaceutically acceptable excipient is L-arginine.

Embodiment P'36: A method of treating a bacterial infection in a subject in need thereof, comprising administering to the subject a pharmaceutical composition of any one of Embodiment P'1-P'19.

Embodiment P'37: A method of treating a bacterial infection in a subject in need thereof, comprising administering to the subject a pharmaceutical composition according to the method of any one of Embodiment P'20-P'35.

Embodiment P'38: The method of any one of Embodiment P'20-P'37, wherein the pharmaceutical composition comprises about 500 mg of (R)-3-(2-(trans-4-(2-aminoethylamino)cyclohexyl)acetamido)-2-hydroxy-3,4-dihydro-2H-benzo[e][1,2]oxaborinine-8-carboxylic acid.

Embodiment P'39: The method of any one of Embodiment P'20-P'37, wherein the pharmaceutical composition comprises about 750 mg of (R)-3-(2-(trans-4-(2-aminoethylamino)cyclohexyl)acetamido)-2-hydroxy-3,4-dihydro-2H-benzo[e][1,2]oxaborinine-8-carboxylic acid.

Embodiment P'40: The method of any one of Embodiment P'20-P'39, wherein the pharmaceutical composition comprises about 2 g of cefepime.

Embodiment P'41: The method of any one of Embodiment P'20-P'10, wherein the pharmaceutical composition is administered by intravenous (IV) infusion.

Embodiment P'42: The method of Embodiment P'41, wherein a period of infusion of the pharmaceutical composition is about 2 hours.

Method of Administration of Intravenous/Intramuscular Administration

In some embodiments, the pharmaceutical composition is administered via intravenous/intramuscular injection. In some embodiments, the pharmaceutical composition is infused into the patient over a period of time. In various embodiments, the infusion time (period of infusion) ranges from 5 minutes to continuous infusion, from 10 minutes to 8 hours, from 30 minutes to 4 hours, and from 1 hour to 3 hours. In one embodiment, the pharmaceutical composition is infused over a 30 minute period. In one embodiment, the pharmaceutical composition is infused over a 1 hour period. In one embodiment, the pharmaceutical composition is infused over a 1.5 hour period. In one embodiment, the pharmaceutical composition is infused over a 2 hour period. In one embodiment, the pharmaceutical composition is infused over a 3 hour period. In one embodiment, the pharmaceutical composition is infused over a 4 hour period. In some embodiments, the infusion is repeated at the desired dose interval, which includes, for example, 6 hours, 8 hours, 12 hours, or 24 hours.

In some embodiments, the pharmaceutical composition is administered for a period of one day. In some embodiments, the pharmaceutical composition is administered over a period of two days. In some embodiments, the pharmaceutical composition is administered over a period of three days. In some embodiments, the pharmaceutical composition is administered over a period of four days. In some embodiments, the pharmaceutical composition is administered over a period of five days. In some embodiments, the pharmaceutical composition is administered over a period of six days. In some embodiments, the pharmaceutical composition is administered over a period of seven days. In some embodiments, the pharmaceutical composition is administered over a period of eight days. In some embodiments, the pharmaceutical composition is administered over a period of nine days. In some embodiments, the pharmaceutical composition is administered over a period of ten days. In some embodiments, the pharmaceutical composition is administered over a period of 11 days. In some embodiments, the pharmaceutical composition is administered over a period of 12 days. In some embodiments, the pharmaceutical composition is administered over a period of 13 days. In some embodiments, the pharmaceutical composition is administered over a period of 14 days. In some embodiments, the pharmaceutical composition is administered over a period of 28 days. In some embodiments, the pharmaceutical composition is administered over a period of 29 days or more.

In some embodiments, the infusion is repeated at the desired dose interval, which includes, for example, 6 hours, 8 hours, 12 hours, or 24 hours for a period of one day. In some embodiments, the infusion is repeated at the desired dose interval, which includes, for example, 6 hours, 8 hours, 12 hours, or 24 hours over a period of two days. In some embodiments, the infusion is repeated at the desired dose interval, which includes, for example, 6 hours, 8 hours, 12 hours, or 24 hours over a period of three days. In some embodiments, the infusion is repeated at the desired dose interval, which includes, for example, 6 hours, 8 hours, 12 hours, or 24 hours over a period of four days. In some embodiments, the infusion is repeated at the desired dose interval, which includes, for example, 6 hours, 8 hours, 12 hours, or 24 hours over a period of five days. In some embodiments, the infusion is repeated at the desired dose interval, which includes, for example, 6 hours, 8 hours, 12 hours, or 24 hours over a period of six days. In some embodiments, the infusion is repeated at the desired dose interval, which includes, for example, 6 hours, 8 hours, 12 hours, or 24 hours over a period of seven days. In some embodiments, the infusion is repeated at the desired dose interval, which includes, for example, 6 hours, 8 hours, 12 hours, or 24 hours over a period of eight days. In some embodiments, the infusion is repeated at the desired dose interval, which includes, for example, 6 hours, 8 hours, 12 hours, or 24 hours over a period of nine days. In some embodiments, the infusion is repeated at the desired dose interval, which includes, for example, 6 hours, 8 hours, 12 hours, or 24 hours over a period of ten days. In some embodiments, the infusion is repeated at the desired dose interval, which includes, for example, 6 hours, 8 hours, 12 hours, or 24 hours over a period of 11 days. In some embodiments, the infusion is repeated at the desired dose interval, which includes, for example, 6 hours, 8 hours, 12 hours, or 24 hours over a period of 12 days. In some embodiments, the infusion is repeated at the desired dose interval, which includes, for example, 6 hours, 8 hours, 12 hours, or 24 hours over a period of 13 days. In some embodiments, the infusion is repeated at the desired dose interval, which includes, for example, 6 hours, 8 hours, 12 hours, or 24 hours over a period of 14 days. In some embodiments, the infusion is repeated at the desired dose interval, which includes, for example, 6 hours, 8 hours, 12 hours, or 24 hours over a period of 28 days. In some embodiments, the infusion is repeated at the desired dose interval, which includes, for example, 6 hours, 8 hours, 12 hours, or 24 hours over a period of 29 days or more. In certain embodiments, only a single infusion is administered on the last day for the treatment period.

In some embodiments, the infusion is repeated every 8 hours for a period of one day. In some embodiments, the infusion is repeated every 8 hours over a period of two days. In some embodiments, the infusion is repeated every 8 hours over a period of three days. In some embodiments, the infusion is repeated every 8 hours over a period of four days. In some embodiments, the infusion is repeated every 8 hours over a period of five days. In some embodiments, the infusion is repeated every 8 hours over a period of six days. In some embodiments, the infusion is repeated every 8 hours over a period of seven days. In some embodiments, the infusion is repeated every 8 hours over a period of eight days. In some embodiments, the infusion is repeated every 8 hours over a period of nine days. In some embodiments, the infusion is repeated every 8 hours over a period of ten days. In some embodiments, the infusion is repeated every 8 hours over a period of 11 days. In some embodiments, the infusion is repeated every 8 hours over a period of 12 days. In some embodiments, the infusion is repeated every 8 hours over a period of 13 days. In some embodiments, the infusion is repeated every 8 hours over a period of 14 days. In some embodiments, the infusion is repeated every 8 hours over a period of 28 days. In some embodiments, the infusion is repeated every 8 hours over a period of 29 days or more. In some embodiments, only one infusion is administered on the last day of the administration period. In some embodiments, the infusion is repeated every 8 hours over a period of 10 days with three doses on days 1-9 and one dose on day 10.

In some embodiments, the infusion is repeated every 12 hours for a period of one day. In some embodiments, the infusion is repeated every 12 hours over a period of two days. In some embodiments, the infusion is repeated every 12 hours over a period of three days. In some embodiments, the infusion is repeated every 12 hours over a period of four days. In some embodiments, the infusion is repeated every 12 hours over a period of five days. In some embodiments, the infusion is repeated every 12 hours over a period of six days. In some embodiments, the infusion is repeated every 12 hours over a period of seven days. In some embodiments, the infusion is repeated every 12 hours over a period of eight days. In some embodiments, the infusion is repeated every 12 hours over a period of nine days. In some embodiments, the infusion is repeated every 12 hours over a period of ten days. In some embodiments, the infusion is repeated every 12 hours over a period of 11 days. In some embodiments, the infusion is repeated every 12 hours over a period of 12 days. In some embodiments, the infusion is repeated every 12 hours over a period of 13 days. In some embodiments, the infusion is repeated every 12 hours over a period of 14 days. In some embodiments, the infusion is repeated every 12 hours over a period of 28 days. In some embodiments, the infusion is repeated every 12 hours over a period of 29 days or more. In some embodiments, only one infusion is administered on the last day of the administration period.

In some embodiments, the infusion is repeated every 24 hours for a period of one day. In some embodiments, the infusion is repeated every 24 hours over a period of two days. In some embodiments, the infusion is repeated every 24 hours over a period of three days. In some embodiments, the infusion is repeated every 24 hours over a period of four days. In some embodiments, the infusion is repeated every 24 hours over a period of five days. In some embodiments, the infusion is repeated every 24 hours over a period of six days. In some embodiments, the infusion is repeated every 24 hours over a period of seven days. In some embodiments, the infusion is repeated every 24 hours over a period of eight days. In some embodiments, the infusion is repeated every 24 hours over a period of nine days. In some embodiments, the infusion is repeated every 24 hours over a period of ten days. In some embodiments, the infusion is repeated every 24 hours over a period of 11 days. In some embodiments, the infusion is repeated every 24 hours over a period of 12 days. In some embodiments, the infusion is repeated every 24 hours over a period of 13 days. In some embodiments, the infusion is repeated every 24 hours over a period of 14 days. In some embodiments, the infusion is repeated every 24 hours over a period of 28 days. In some embodiments, the infusion is repeated every 24 hours over a period of 29 days or more.

In some embodiments, the infusion is repeated every 48 hours over a period of two days. In some embodiments, the infusion is repeated every 48 hours over a period of four days. In some embodiments, the infusion is repeated every 48 hours over a period of six days. In some embodiments, the infusion is repeated every 48 hours over a period of eight days. In some embodiments, the infusion is repeated every 48 hours over a period of ten days. In some embodiments, the infusion is repeated every 48 hours over a period of 12 days. In some embodiments, the infusion is repeated every 48 hours over a period of 14 days. In some embodiments, the infusion is repeated every 48 hours over a period of 28 days or more.

In some embodiments, the pharmaceutical composition comprises 100 to 5000 mg of cefepime. In some embodiments, the pharmaceutical composition comprises 250 to 2000 mg of cefepime. In some embodiments, the pharmaceutical composition comprises 250, 300, 350, 400, 450, 500, 550, 600, 650, 700, 750, 800, 850, 900, 950, 1000, 1100, 1200, 1300, 1400, 1500, 1600, 1700, 1800, 1900, or 2000 mg of cefepime. In some embodiments, the pharmaceutical composition comprises 250 mg of cefepime. In some embodiments, the pharmaceutical composition comprises 500 mg of cefepime. In some embodiments, the pharmaceutical composition comprises 750 mg of cefepime. In some embodiments, the pharmaceutical composition comprises 1000 mg of cefepime. In some embodiments, the pharmaceutical composition comprises 1250 mg of cefepime. In some embodiments, the pharmaceutical composition comprises 1500 mg of cefepime. In some embodiments, the pharmaceutical composition comprises 1750 mg of cefepime. In some embodiments, the pharmaceutical composition comprises 2000 mg of cefepime.

In some embodiments, the daily dose of cefepime is 250 mg to 12 g. In some embodiments, the daily dose of cefepime is 250 mg, 500 mg, 750, mg, 1000, mg, 1250 mg, 1500 mg, 1750 mg, 2000 mg, 2250 mg, 2500 mg, 2750 mg, 3000 mg, 3.5 g, 4 g, 4.5 g, 5 g, 5.5 g, 6 g, 6.5 g, 7 g, 7.5 g, 8 g, 8.5 g, 9 g, 9.5 g, or 10 g. In some embodiments, the daily dose of cefepime is 250 mg. In some embodiments, the daily dose of cefepime is 500 mg. In some embodiments, the daily dose of cefepime is 1 g. In some embodiments, the daily dose of cefepime is 2 g. In some embodiments, the daily dose of cefepime is 4 g. In some embodiments, the daily dose of cefepime is 6 g. In some embodiments, the daily dose of cefepime is 8 g. In some embodiments, the daily dose of cefepime is 10 g. In some embodiments, the daily dose of cefepime is 12 g.

In some embodiments, the pharmaceutical composition comprises 100 to 2000 mg of Compound 1. In some embodiments, the pharmaceutical composition comprises 125 to 1000 mg of Compound 1. In some embodiments, the pharmaceutical composition comprises 125, 187.5, 200, 250, 300, 350, 375, 400, 450, 500, 550, 600, 650, 700, 750, 800, 850, 900, 950, or 1000 mg of Compound 1. In some embodiments, the pharmaceutical composition comprises 100 mg of Compound 1. In some embodiments, the pharmaceutical composition comprises 125 mg of Compound 1. In some embodiments, the pharmaceutical composition comprises 150 mg of Compound 1. In some embodiments, the pharmaceutical composition comprises 187.5 mg of Compound 1. In some embodiments, the pharmaceutical composition comprises 200 mg of Compound 1. In some embodiments, the pharmaceutical composition comprises 250 mg of Compound 1. In some embodiments, the pharmaceutical composition comprises 300 mg of Compound 1. In some embodiments, the pharmaceutical composition comprises 350 mg of Compound 1. In some embodiments, the pharmaceutical composition comprises 375 mg of Compound 1. In some embodiments, the pharmaceutical composition comprises 400 mg of Compound 1. In some embodiments, the pharmaceutical composition comprises 450 mg of Compound 1. In some embodiments, the pharmaceutical composition comprises 500 mg of Compound 1. In some embodiments, the pharmaceutical composition comprises 550 mg of Compound 1. In some embodiments, the pharmaceutical composition comprises 600 mg of Compound 1. In some embodiments, the pharmaceutical composition comprises 650 mg of Compound 1. In some embodiments, the pharmaceutical composition comprises 750 mg of Compound 1. In some embodiments, the pharmaceutical composition comprises 800 mg of Compound 1. In some embodiments, the pharmaceutical composition comprises 850 mg of Compound 1. In some embodiments, the pharmaceutical composition comprises 900 mg of Compound 1. In some embodiments, the pharmaceutical composition comprises 950 mg of Compound 1. In some embodiments, the pharmaceutical composition comprises 1000 mg of Compound 1.

In some embodiments, the pharmaceutical composition comprises 100 to 2000 mg of Compound 1 and 0.5 to 5 g of cefepime. In certain embodiments, the pharmaceutical composition comprises 125 to 1000 mg of Compound 1 and 0.5 to 2.5 g of cefepime. In some embodiments, the pharmaceutical composition comprises 125, 150, 187.5, 200, 250, 300, 350, 400, 450, 500, 550, 600, 650, 700, 750, 800, 850, 900, 950, or 1000 mg of Compound 1 and 250, 300, 350, 400, 450, 500, 550, 600, 650, 700, 750, 800, 850, 900, 950, or 1000 mg of Compound 1. In certain embodiments, the pharmaceutical composition comprises 250 mg of Compound 1 and 2 g of cefepime. In some embodiments, the pharmaceutical composition comprises 500 mg of Compound 1 and 2 g of cefepime. In certain embodiments, the pharmaceutical composition comprises 750 mg of Compound 1 and 2 g of cefepime. In certain embodiments, the pharmaceutical composition comprises 125 mg of Compound 1 and 1 g of cefepime. In some embodiments, the pharmaceutical composition comprises 250 mg of Compound 1 and 1 g of cefepime. In certain embodiments, the pharmaceutical composition comprises 375 mg of Compound 1 and 1 g of cefepime. In certain embodiments, the pharmaceutical composition comprises 62.5 mg of Compound 1 and 2 g of cefepime. In some embodiments, the pharmaceutical composition comprises 125 mg of Compound 1 and 2 g of cefepime. In certain embodiments, the pharmaceutical composition comprises 187.5 mg of Compound 1 and 2 g of cefepime.

In some embodiments, the daily dose of Compound 1 is about 200 mg to 5 g. In some embodiments, the daily dose of Compound 1 is about 200, 250 mg, 500 mg, 750, mg, 1000, mg, 1250 mg, 1500 mg, 1750 mg, 2000 mg, 2250 mg, 2500 mg, 2750 mg, 3000 mg, 3.5 g, 4 g, 4.5 g, or 5 g. In some embodiments, the daily dose of compound 1 is 250 mg. In some embodiments, the daily dose of compound 1 is 500 mg. In some embodiments, the daily dose of compound 1 is 750 mg. In some embodiments, the daily dose of compound 1 is 1000 mg. In some embodiments, the daily dose of compound 1 is 1250 mg. In some embodiments, the daily dose of compound 1 is 1500 mg. In some embodiments, the daily dose of compound 1 is 1750 mg. In some embodiments, the daily dose of compound 1 is 2000 mg. In some embodiments, the daily dose of compound 1 is 2250 mg. In some embodiments, the daily dose of compound 1 is 2500 mg. In some embodiments, the daily dose of compound 1 is 2750 mg. In some embodiments, the daily dose of compound 1 is 3000 mg. In some embodiments, the daily dose of compound 1 is 3.5 g. In some embodiments, the daily dose of compound 1 is 4 g. In some embodiments, the daily dose of compound 1 is 4.5 g. In some embodiments, the daily dose of compound 1 is 5 g.

In some embodiments, the pharmaceutical composition is stored in a sterile container. In some embodiments, Compound 1, a pharmaceutically acceptable salt, a solvate, or a pharmaceutically acceptable salt and solvate thereof is co-administered with an antibiotic. In some embodiments, the antibiotic is a beta-lactam antibiotic. In some embodiments, the beta-lactam antibiotic is cefepime.

In some embodiments, Compound 1, a pharmaceutically acceptable salt, a solvate, or a pharmaceutically acceptable salt and solvate thereof and cefepime are provided in separate containers. In some embodiments, Compound 1, a pharmaceutically acceptable salt, a solvate, or a pharmaceutically acceptable salt and solvate thereof and cefepime are provided in a single container. In some embodiments, the container is an IV bag. In some embodiments, the container is a glass bottle. In some embodiments, the container is an amber glass bottle.

Disclosed herein is a method of administering to a subject in need thereof, a pharmaceutical composition comprising:
(i) (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof; and
(ii) cefepime.

In some embodiments of a method of administering a pharmaceutical composition, the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof, and the cefepime are formulated in separate containers. In some embodiments of a method of administering a pharmaceutical composition, (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is in the form of a crystalline form as disclosed herein. In some embodiments of a method of administering a pharmaceutical composition, the crystalline form is Form 1. In some embodiments of a method of administering a pharmaceutical composition, the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is formulated in a first container. In some embodiments of a method of administering a pharmaceutical composition, the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is in the form of a first powder for reconstitution. In some embodiments of a method of administering a pharmaceutical composition, the cefepime is formulated in a second container. In some embodiments of a method of administering a pharmaceutical composition, the cefepime is in the form of a second powder for reconstitution.

In some embodiments of a method of administering a pharmaceutical composition, the method comprises:
(a) mixing the first powder for reconstitution and the second powder for reconstitution to obtain a third powder for reconstitution;
(b) reconstituting the third powder for reconstitution of step (a) with an aqueous carrier to obtain a homogeneous liquid; and
(c) administering the homogeneous liquid of step (b) to the subject in need thereof.

In some embodiments of a method of administering a pharmaceutical composition, the method comprises:
(a) reconstituting the first powder for reconstitution with a first aqueous carrier to obtain a first homogeneous liquid;
(b) reconstituting the second powder for reconstitution with a second aqueous carrier to obtain a second homogeneous liquid;
(c) mixing the first homogeneous liquid of step (a) and the second homogeneous liquid of step (b) to obtain a third homogeneous liquid; and
(d) administering the third homogeneous liquid of step (c) to the subject in need thereof.

In some embodiments of a method of administering a pharmaceutical composition, each of the aqueous carrier is independently water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof. In some embodiments of a pharmaceutical composition, the composition further comprises a pharmaceutically acceptable excipient. In some embodiments of a pharmaceutical composition, the pharmaceutically acceptable excipient is an amino acid or a monosaccharide derivative. In some embodiments of a pharmaceutical composition, the pharmaceutically acceptable excipient is L-arginine. In some embodiments of a pharmaceutical composition, the pharmaceutically acceptable excipient is meglumine.

Also disclosed herein is a method of administering to a subject in need thereof, a pharmaceutical composition comprising:
(i) (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt or a solvate thereof; and
(ii) cefepime.

In some embodiments of a method of administering a pharmaceutical composition, the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof, and the cefepime are formulated in a single container. In some embodiments of a method of administering a pharmaceutical composition, (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof is in the form of a crystalline form as disclosed herein. In some embodiments of a method of administering a pharmaceutical composition, the crystalline form is Form 1. In some embodiments of a method of administering a pharmaceutical composition, the (R)-3-(2-(trans-4-(2-aminoethylamino)cyclohexyl)acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof, and the cefepime are in the form of a powder for reconstitution. In some embodiments of a method of administering a pharmaceutical composition, the method comprises:

(a) reconstituting the powder for reconstitution with an aqueous carrier to obtain a homogeneous liquid; and
(b) administering the homogeneous liquid of step (a) to the subject in need thereof.

In some embodiments of a method of administering a pharmaceutical composition, the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof. In some embodiments of a pharmaceutical composition, the composition further comprises a pharmaceutically acceptable excipient. In some embodiments of a pharmaceutical composition, the pharmaceutically acceptable excipient is an amino acid or a monosaccharide derivative. In some embodiments of a pharmaceutical composition, the pharmaceutically acceptable excipient is L-arginine. In some embodiments of a pharmaceutical composition, the pharmaceutically acceptable excipient is meglumine.

Methods of Treatment

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with Compound 1, a pharmaceutically acceptable salt, a solvate, or a pharmaceutically acceptable salt and solvate thereof. In some embodiments, the bacteria to be inhibited by administration of Compound 1, a pharmaceutically acceptable salt, a solvate thereof, or a pharmaceutically acceptable salt and solvate thereof are bacteria that are resistant to beta-lactam antibiotics. The term "resistant" is well-understood by those of ordinary skill in the art (see, e g Payne et al., Antimicrobial Agents and Chemotherapy 38 767-772 (1994), Hanaki et al., Antimicrobial Agents and Chemotherapy 30 1120-1126 (1995)).

These methods are useful for inhibiting bacterial growth in a variety of contexts. In certain embodiments, Compound 1, a pharmaceutically acceptable salt, a solvate, or a pharmaceutically acceptable salt and solvate thereof is administered to an experimental cell culture in vitro to prevent the growth of beta-lactam resistant bacteria. In certain other embodiments, Compound 1, a pharmaceutically acceptable salt, a solvate, or a pharmaceutically acceptable salt and solvate thereof is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, an antibiotic is co-administered with the beta-lactamase inhibitor. In some embodiments, the antibiotic is a beta-lactam antibiotic. In some embodiments, the beta-lactam antibiotic is cefepime.

In another aspect provided herein are methods of treating a bacterial infection, which method comprises administering to a subject a pharmaceutical composition comprising Compound 1, a pharmaceutically acceptable salt, a solvate, or a pharmaceutically acceptable salt and solvate thereof, and a pharmaceutically acceptable excipient as described above. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Elizabethkingia meningoseptica, Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, or Staphylococcus saccharolyticus.*

In some embodiments, the infection that is treated or prevented comprises a bacteria that includes *Elizabethkingia meningoseptica, Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter* coli, *Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

In one aspect, presented herein is a method of treating bacterial infections by administration of Compound 1, a pharmaceutically acceptable salt, a solvate, or a pharmaceutically acceptable salt and solvate thereof in combination with a beta-lactam antibiotic. In some embodiments, the beta-lactam antibiotic is cefepime. In certain embodiments, the bacterial infection is complicated intra-abdominal infection, complicated urinary tract infection (including pyelonephritis), pneumonia, uncomplicated urinary tract infections, or uncomplicated skin and skin structure infection. In certain embodiments, the bacterial infection is complicated intra-abdominal infection, or complicated urinary tract infection (including pyelonephritis). In certain embodiments, the bacterial infection is complicated intra-abdominal infection. In certain embodiments, the bacterial infection is complicated urinary tract infection (including pyelonephritis).

In another aspect, presented herein is a method of treating febrile neutropenic patients by administration of Compound 1, a pharmaceutically acceptable salt, a solvate, or a pharmaceutically acceptable salt and solvate thereof in combination with a beta-lactam antibiotic. In some embodiments, the beta-lactam antibiotic is cefepime.

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a," "an," and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. "Administering" a pharmaceutical composition may be accomplished by injection, topical administration, and oral administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows.

By "pharmaceutically acceptable," it is meant the carrier, diluent or excipient must be compatible with the other ingredients of the composition and not deleterious to the recipient thereof.

The term "pharmaceutical composition" means a composition comprising at least one active ingredient, such as Compound 1, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "substantially the same as" as used herein, refers to a powder x-ray diffraction pattern or differential scanning calorimetry pattern that is non-identical to those depicted herein, but that falls within the limits of experimental error, when considered by one of ordinary skill in the art.

EXAMPLES

Analytical Methods

X-Ray Powder Diffraction

XRPD patterns were obtained using the high-throughput XRPD (HT-XRPD) set-up. The plates were mounted on a Bruker GADDS diffractometer equipped with a Hi-Star area detector. The XRPD platform was calibrated using Silver Behenate for the long d-spacings and Corundum for the short d-spacings.

Data collection was carried out at room temperature using monochromatic CuKα radiation in the 2θ region between 1.5° and 41.5°, which is the most distinctive part of the XRPD pattern. The diffraction pattern of each well was collected in two 2 θ ranges (1.5°≤2θ21.5° for the first frame, and 19.5°≤2θ 41.5° for the second) with an exposure time of 90 s for each frame. No background subtraction or curve smoothing was applied to the XRPD patterns.

The carrier material used during XRPD analysis was transparent to X-rays and contributed only slightly to the background.

High Resolution X-Ray Powder Diffraction (HR-XRPD)

The powder data were collected on D8 Advance diffractometer using Cu Kα1 radiation (1.54016 Å) with germanium monochromator at Room Temperature. The data were collected in 2 θ alone (detector scan) mode from 4 to 45° 2 θ with 0.016° 2 θ steps, 3426.5 s per step on solid state LynxEye detector. The sample was measured in 8 mm long glass capillary with 0.5 mm outer diameter.

Variable Temperature X-Ray Powder Diffraction (VT-XRPD)

For variable temperature experiments the ANSYCO HT chamber was used, installed within the D8 Advance system diffractometer (Bruker) designed with Brag-Brentano geometry and equipped with LynxEye solid state detector. The radiation used for collecting the data was CuKα1 (λ=1.54056 A) monochromatized by germanium crystal. The material was placed on a fixed sample holder that was mounted inside the chamber.

VT-XRPD: The temperature variation rate was 10° C./min. The patterns were collected in the range 9-24.5 2θ, with a step of 0.01569 2θ and measuring time per step of 8 sec. The data collection time, per temperature, was 2*60 min.

Differential Scanning Calorimetry (DSC) Analysis

Melting properties were obtained from DSC thermograms, recorded with a heat flux DSC822e instrument (Mettler-Toledo GmbH, Switzerland). The DSC822e was calibrated for temperature and enthalpy with a small piece of indium (melting point at 156.6 C; ΔHf=28.45 J·g−1). Samples were sealed in standard 40 μl aluminum pans, pin-holed and heated in the DSC from 25° C. to 300° C., at a heating rate of 10° C. min−1. Dry N2 gas, at a flow rate of 50 ml min−1 was used to purge the DSC equipment during measurement.

Thermogravimetric Analysis Coupled With Mass Spectroscopy (TGMS)

Mass loss due to solvent or water loss from the crystals was determined by TGA/SDTA (TGA: thermogravimetric analysis; SDTA: single differential thermal analysis). Monitoring the sample weight, during heating in a TGA/SDTA851e instrument (Mettler-Toledo GmbH, Switzerland), resulted in a weight vs. temperature curve. The TGA/SDTA85 1e was calibrated for temperature with indium and aluminum. Samples were weighed into 100 μaluminum crucibles and sealed. The seals were pin-holed and the crucibles heated in the TGA from 25 to 300 or 400° C. (depending on the experiment) at a heating rate of 10° C. min−1. Dry N2 gas was used for purging.

The gases evolved from the TGA samples were analyzed by a mass spectrometer Omnistar GSD 301 T2 (Pfeiffer Vacuum GmbH, Germany). The latter is a quadrupole mass spectrometer, which analyzes masses in the range of 0-200 amu.

Dynamic Vapor Sorption (DVS) Analysis

Differences in hygroscopicity (moisture uptake) of the various forms of a solid material provided a measure of their relative stability at increasing relative humidity. Moisture sorption isotherms of small samples were obtained using a DVS-1 system from Surface Measurement Systems (London, UK); this instrument is suitable for use with as little as a few milligrams of sample, with an accuracy of 0.1 μg.

The following humidity profile was applied: The relative humidity was cycled from 45% to 95% (sorption), back to 0% (desorption) and to 45%, at a constant temperature of 25° C. Steps consisted of 10% RH (between 45% and 75% RH), 5% RH (between 0and 45% RH) and 20% (between 75% and 95% RH). Weight equilibration per step was set with a minimum holding time of 1 hour. At the end of the DVS experiments, the recovered solid material was measured by HT-XRPD.

Example 1: Preparation of Compound 1-Dihydrochloride Salt

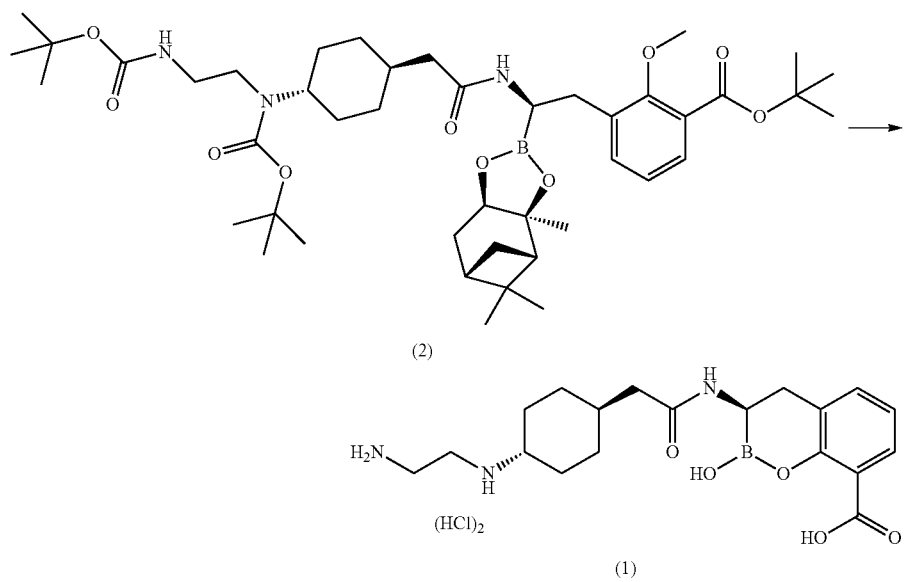

To a solution of tert-butyl 3-((R)-2-(2-((1r,4R)-4-((tert-butoxycarbonyl)(2-((tert-butoxycarbonyl)amino)ethyl)amino)cyclohexyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (Structure 2, 110.9 g, 136.7 mmol) in 1,4 dioxane (137 mL) was added hydrochloric acid (540 mL, 3M in water). The resulting mixture was heated to reflux and stirred at this temperature for 100 minutes. The resulting mixture was cooled to room temperature over 30 minutes then extracted with methyl tert-butyl ether (3×200 mL). The aqueous phase was concentrated under vacuum (57-29 mmHg and 20-72° C. external bath temperature). The residue was diluted to a total weight of 130 g with water. To this solution was added isopropanol (90 mL) over approximately 10 minutes. This solution was seeded with Compound 1-(HCl)$_2$ crystals (100 mg). To this mixture was added isopropanol (100 mL) over approximately 5 minutes. The resulting slurry was stirred for approximately 15 hours then filtered under vacuum, the solid was washed with isopropanol (2×200 mL) then methyl tert-butyl ether (400 mL). The solid was further dried under high vacuum to give the title compound (structure 1) (43.9 g) as a white crystalline solid as a mixture of Form 1 and Form 2.

Example 2: Compound 1-Dihydrochloride Crystalline Forms

Example 2a: Solubility of Compound 1-Dihydrochloride in Ipa/Water Mixtures

Figure 1B:
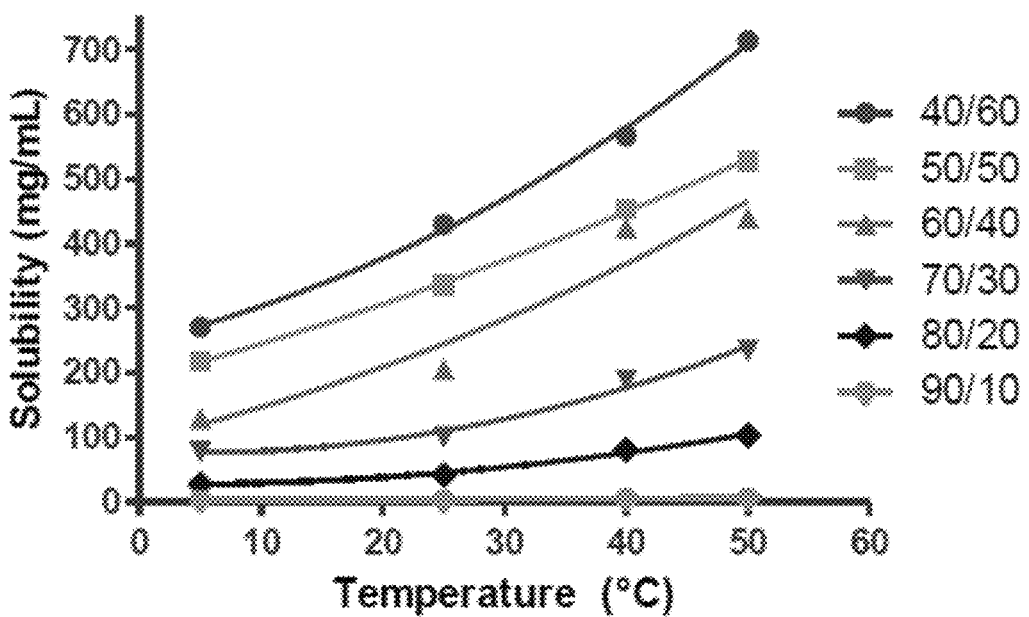
FIG. 1B shows the solubility values of Compound 1-dihydrochloride in IPA/water mixtures as function of the temperature.

In order to design a re-crystallization process for Compound 1-dihydrochloride salt from water as solvent and IPA as anti-solvent, the solubility of the API in these combinations were determined. Suspensions in various water/IPA mixtures were prepared and incubated for 24 hours at 5°, 25°, 40° and 50° C. Upon completion of the incubation time the solids were separated from the mother liquors by centrifugation and filtration and the concentration of Compound 1 in solution was determined by HPLC analysis. The remaining solids were analyzed by HT-XRPD. The results of the solubility determination as function of anti-solvent content and temperature is presented in Table 6 and in FIG. 1A and FIG. 1B.

TABLE 6

Solubility values of Compound 1-dihydrochloride in mg/ml in IPA/water mixtures at four temperatures, 5° C., 25° C., 40° C., 50° C.

| Solvent mixture | Temperatures | | | |
|---|---|---|---|---|
| | 5° C. | 25° C. | 40° C. | 50° C. |
| IPA/H$_2$O (40:60) | 270.7 | 429.4 | 566.7 | 713.8 |
| IPA/H$_2$O (50:50) | 217.3 | 335.9 | 453.9 | 528.4 |
| IPA/H$_2$O (60:40) | 128.9 | 205.4 | 424.2 | 439.5 |
| IPA/H$_2$O (70:30) | 78.6 | 100.9 | 189.2 | 235.0 |
| IPA/H$_2$O (80:20) | 28.0 | 41.7 | 81.0 | 102.5 |
| IPA/H$_2$O (90:10) | 4.2 | 4.2 | 5.6 | 7.2 |

Example 2B: Preparation of Crystalline Compound 1-Dihydrochloride

To Compound 1-dihydrochloride from example 1, (675 g, Sample A) was added 1.85 L of isopropanol/water (40/60 v/v). The mixture was stirred at 19 to 26° C. until a clear solution was obtained. The solution was filtered through a membrane filter (5 micron). To the filtrate was added isopropanol (550 mL) followed by seed crystals (6.75 g). To this mixture was added isopropanol (8.7 L) over 1 hour. The resulting mixture was stirred for 63 hours then filtered under vacuum. The wet cake was deliquored under vacuum for 1 hour 20 minutes. The solid was washed with isopropanol (700 mL) then methyl teat-butyl ether (700 mL). The solid was dried under a flow of ambient air over 2 hours 45 minutes. Recovered 612 g of Compound 1-dihydrochloride monohydrate (Sample B). Chloride by ion chromatography 14.8% w/w. Water content by Karl Fischer analysis=3.8% w/w.

Example 2C: Impurity Profile of Crystalline Compound 1-Dihydrochloride Monohydrate Table 7 shows the impurity profile of Compound 1-dihydrochloride (Sample A) and crystalline Compound 1-dihydrochloride (Sample B) as assessed by HPLC method described in Table 8.

TABLE 7

| SAMPLE | Comp. 1 | RRT_0.86 | RRT_1.06 | RRT_1.15 | RRT_1.21 | RRT_1.26 |
|---|---|---|---|---|---|---|
| Sample A | 97.5 | 0.4 | 0.7 | 0.18 | 0.7 | 0.55 |
| Sample B | 99.7 | 0.16 | Below LOQ | 0.1 | Below LOQ | Below LOQ |

TABLE 8

| Column Details | Zorbax SB-C18 | | |
|---|---|---|---|
| Column Length | 15 cm | | |
| Column Internal Diameter | 4.6 mm | | |
| Column Particle Size | 5 µm | | |
| Mobile Phase A | 0.05 % v/v TFA in water | | |
| Mobile Phase B | 0.05 % v/v TFA in acetonitrile | | |
| Gradient | Time | % A | % B |
| | 0 | 98 | 2 |
| | 15 | 2 | 98 |
| | 20 | 2 | 98 |
| | 20.01 | 98 | 2 |
| | 25 | 98 | 2 |
| Dissolving Solvent | Ultrapure water Type 1 | | |
| Flow | 1.0 mL/min | | |
| Column temperature | 40° C. | | |
| Wavelength | 210 nm | | |
| Injection volume | 5 µL | | |
| Sample concentration | 0.3 mg/mL | | |
| Total run time | 25 min | | |
| Typical retention time | Compound 1: 4.9 min | | |
| Calculations | Relative Retention Time of Peak X (RRT_X): Retention time of Peak X/Retention time of Compound 1 Purity (% area): (Compound 1 Peak Area)/(Σ Peak Area) × 100% Impurity (% area): Impurity Peak area/(Σ Peak Area) × 100% Where Σ Peak Area is the arithmetic sum of all peak areas | | |

Abbreviations:
RRT = relative retention time;
TFA = Trifluoroacetic acid

Example 2D: Xrpd Characterization

Crystalline Compound 1-dihydrochloride (from example 2B) was analyzed by HR-XRPD (FIG. 2). Based on the single crystal data available for the monohydrate (FIG. 3) it was concluded that the crystalline form represents the monohydrate of the dihydrochloride salt of Compound 1. It was called Form 1. Table 1 lists the peaks positions and their intensities for Form 1.

Example 2E: TG/MS and DSC Analysis

Figure 4:
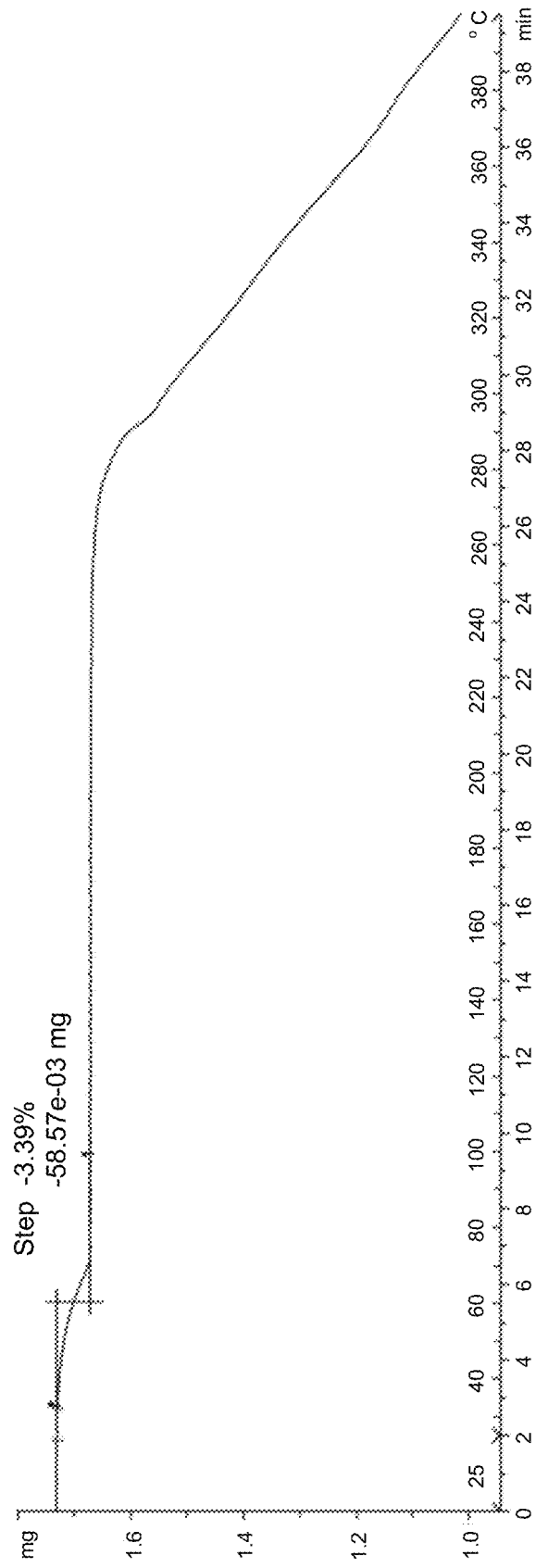
FIG. 4 shows the TGMS thermogram (with heating rate of 10° C./min) of Form 1.

Analysis of Compound 1-dihydrochloride monohydrate by TG/MS (FIG. 4) showed that a 3.4% mass loss was recorded between 25° and 80° C. This mass is attributed to the loss of 1 molecule of water per molecule of Compound 1-dihydrochloride. This result confirms the XRPD analysis that the material consisted of the monohydrated form. The compound decomposed at temperatures over 280° C.

Figure 5:
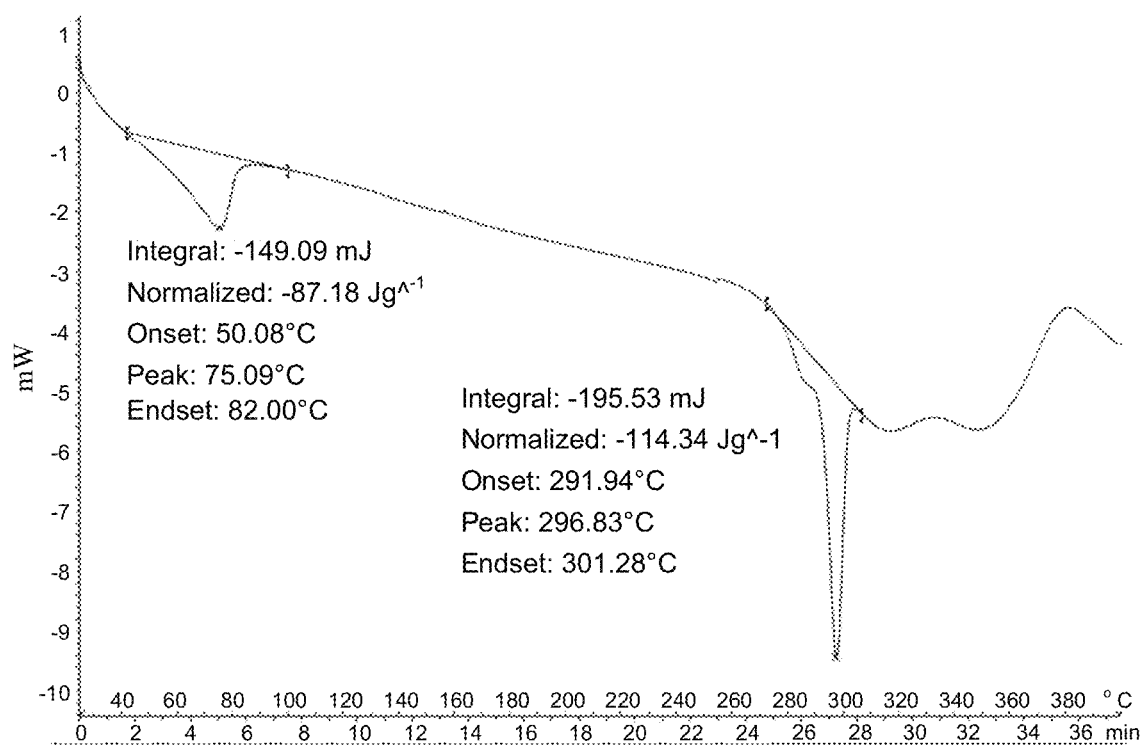
FIG. 5 shows the DSC thermogram (with heating rate of 10° C./min) of Form 1.

FIG. 5 shows the DSC trace of Form 1 for a programmed increase in temperature from 0° C. to 400° C. The DSC trace shows an endothermic event with an onset temperature of approximately 50° C. This event corresponds to the onset of dehydration of the monohydrate. This dehydration process is followed by the decomposition of the compound at about 290° C. signaled by a large endothermic event. It is concluded from this experiment that Form 1 is stable to elevated temperature, up to approximately 50° C.

Example 2F: Dynamic Vapor Sorption Analysis

Figure 6:
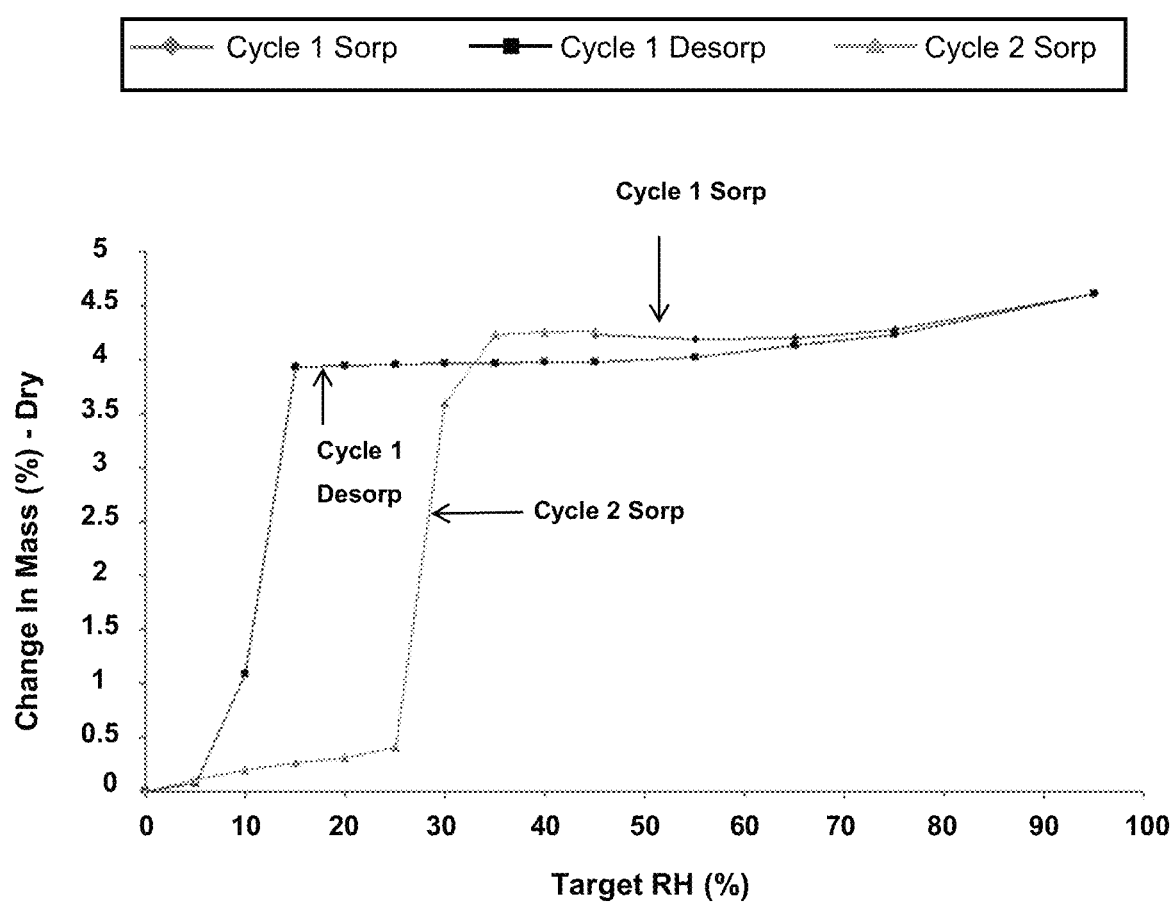
FIG. 6 shows the DVS isothermal of Form 1.

Compound 1-dihydrochloride monohydrate was analyzed by dynamic vapor sorption (FIG. 6). The material was subjected to an isothermal desorption/sorption profile starting at 45%-95%-0%-45% relative humidity levels (step 5% at low relative humidity (RH)) at 25° C.

The temperature was maintained constant at approximately 25° C. for the duration of the experiment. The curve with the diamond markers shows the change in mass of a sample of Form 1 when exposed to increasing relative humidity level (45% RH to 95%). It can be seen that the mass uptake is rather small and that at high humidity level Compound 1-dihydrochloride remained as Form 1. This is confirmed by the mass stability and the VH-XRPD experiment conducted (see FIG. 7).

The curve with the square markers shows the change in mass of a sample of Form 1 when subjected to a series of decreasing relative humidities from 95% RH to 0% RH. It can be seen that the sample mass does not change significantly between approximately 55% RH to 15% RH. Upon subsequent exposure to humidity values of 10, 5, and 0% RH, the sample loses approximately 4% of its mass which corresponds to the loss of a single molecule of water per Compound 1-dihydrochloride salt. A VH-XRPD experiment confirmed that the loss of water was accompanied by a transformation to the anhydrous form (Form 2) (see FIG. 7).

The curve with the triangle markers shows the change in the mass of Form 2 produced by the dehydration of crystalline Form 1, when exposed to increasing relative humidity (0% RH to 50% RH). There is a slight increase in mass up to 25% RH, followed by a sharp increase in mass when Form 2 was exposed to 30% RH. A VH-XRPD experiment showed that Form 2 converts to Form 1 at % RH values in the 25-35% RH range (see FIG. 7). These observations demonstrate that Form 2 undergoes significant changes in moisture content and physical form at relative humidity values that are representative of values specified in pharmaceutical manufacturing facilities.

Example 2G: Variable Humidity XRPD Analysis

To confirm the hypothesis of a solid form change between 40% and 0% relative humidity levels a variable humidity XRPD (VH-XRPD) analysis was performed. The sample was subjected to a humidity profile of 45-75-20-15-10-30-35-45% relative humidity levels at 30° C. At each step, two diffractograms were recorded. The first diffractogram was recorded when the target humidity was reached and the second after the sample had equilibrated for 1 hour at each humidity level. When a phase change occurred and if the conversion rate was faster than the scan time, the diffractogram showed peaks of the starting form at the start (low 2θ angles) and peaks of the converted form at the end of the diffractogram (higher 2θ angles). The most intense peaks of Form 1 (dihydrochloride monohydrate) are in the range between 9.5 and 24.5° 2θ.

Figure 7:
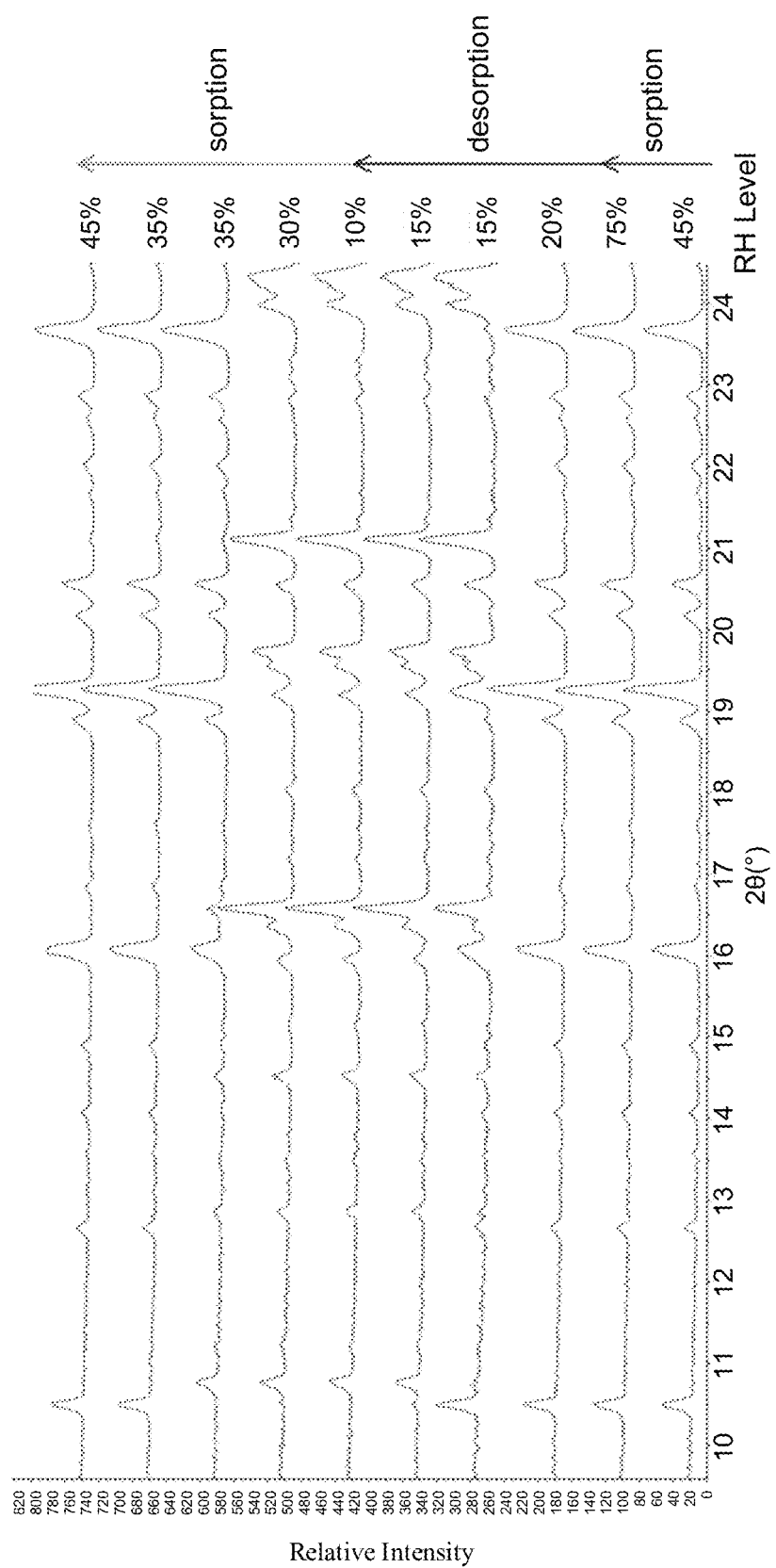
FIG. 7 shows the stacked XRPD diffractograms of Compound 1-dihydrochloride with RH (relative humidity) variation.

The stacked diffractograms recorded at different relative humidity levels are shown in FIG. 7. The measured RH level and the kind of ongoing RH variation step (sorption or desorption) is found on the right hand side. The material displays a clear change in diffractogram indicating a moisture sorption induced phase transition. Upon desorption, the material was converted between 20% and 15% relative humidity to Form 2, the anhydrous form. Upon sorption, Form 2 converted back to Form 1 between 30% and 35% relative humidity. DVS analysis showed a significant moisture sorption in the range between 40% and 95% RH. The VH-XRPD results did not raise evidence for additional form changes at these values.

Example 2H: Characterization of Form 2

Figure 9:
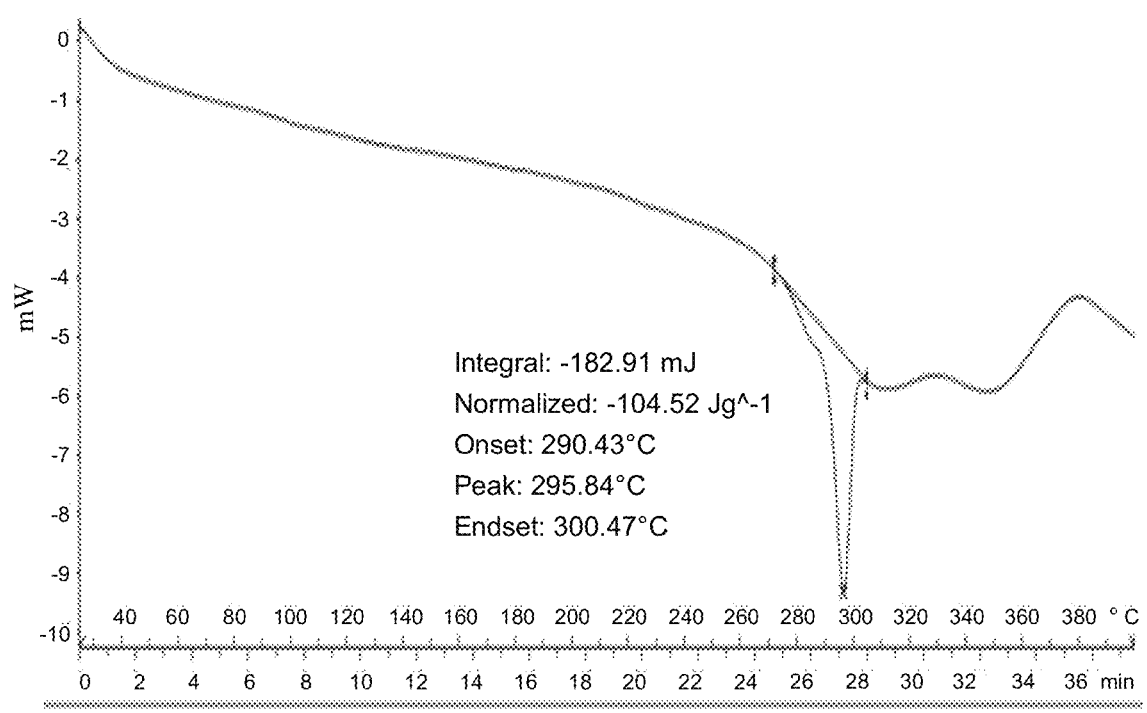
FIG. 9 shows the DSC thermogram of Form 2.

From the variable-humidity X-ray powder diffraction experiments performed on Form 1 a second crystalline form of Compound 1-dihydrochloride was discovered. This form was designated Form 2. For further characterization of Form 2, some material was prepared by vacuum drying Form 1 at 40° C. for 18 hours. FIG. 8 shows the XRPD diffractogram of Form 2. Analysis of a solid sample of Form 2 by TGA demonstrated the anhydrous nature of this solid. The thermogravimetric and the thermogram obtained by DSC analysis showed the absence of any thermal events before decomposition at 280° C. and the absence of any weight loss on drying (FIG. 9). Table 2 lists the peaks positions and their intensities for Form 2.

Figure 10A:
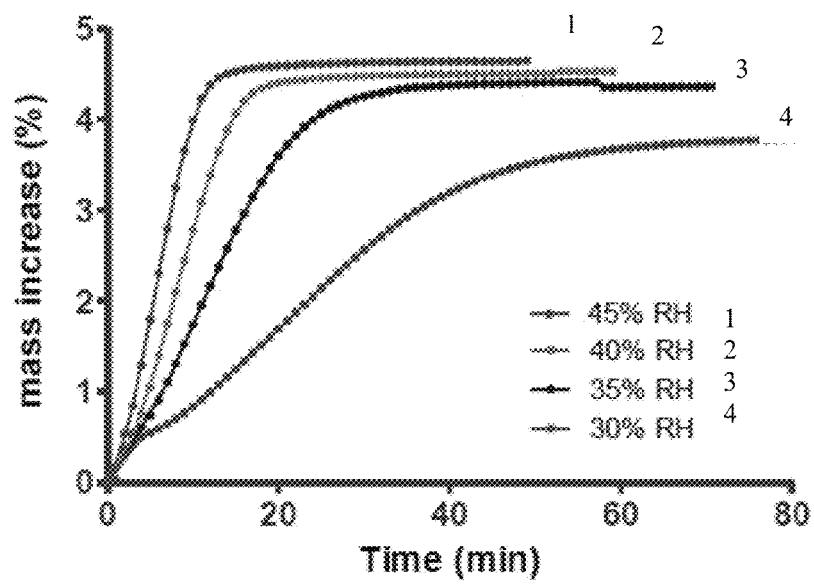
FIG. 10A shows the recorded mass changes as a function of the relative humidity level. Solid samples of Form 2 were incubated at the indicated relative humidity value at 25° C. while the mass changes were continuously recorded.
Figure 10B:
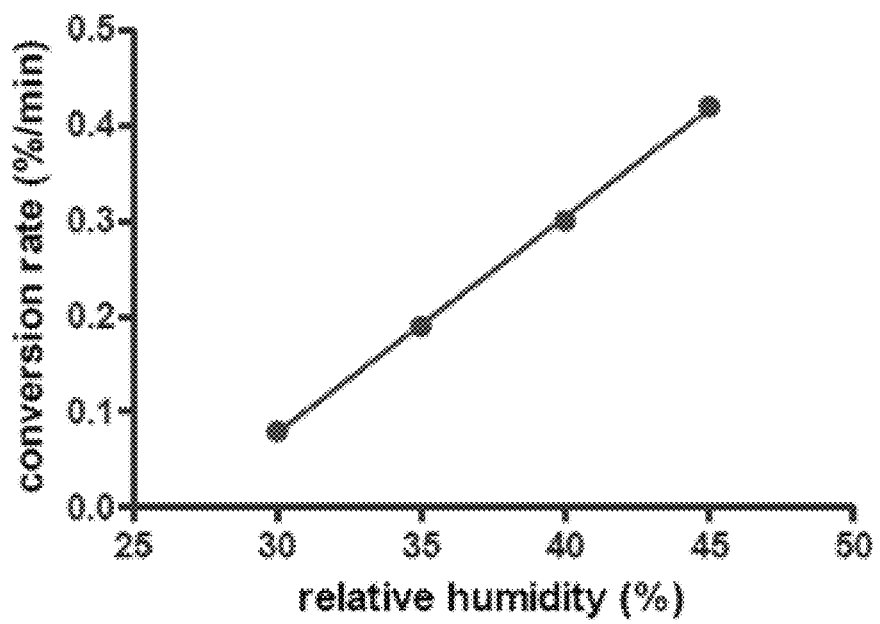
FIG. 10B shows the recorded mass changes as function of the relative humidity level. Conversion rates were calculated and plotted against the relative humidity value (from the linear part of the curve of FIG. 10A). The regression coefficient of the line is 0.9995.

The VH-XRPD and DVS analysis performed on the starting materials suggested that there is a dynamic and reversible relationship between the anhydrous Form 2 and the monohydrate Form 1. The conversion rate of Form 2 to Form 1 as function of the relative humidity value was investigated by a isothermal moisture sorption experiment at fixed relative humidity values. In brief, a solid sample of Form 2 was prepared by drying Form 1. This sample was placed in the DVS machine and incubated for 1 hour at the indicated humidity level while the weight change was recorded. The results are presented in FIG. 10A and FIG. 10B. The conversion rate depended on the relative humidity level. The highest rate was achieved at 45% RH whereas the lowest rate was achieved at 30% RH. The right panel shows the linear relationship between the applied humidify level and the conversion rate.

Summary

Compound 1-dihydrochloride was physically characterized by X-ray powder diffraction, thermal analysis, and dynamic vapor sorption techniques. Loss-on-drying studies performed by TG/MS analysis demonstrated that the material consisted of the monohydrated crystalline solid form of Compound 1-dihydrochloride. This particular form was designated Form 1. The material showed decomposition at temperatures above 280° C. Characterization by DVS analysis showed a dehydration/hydration pattern between 0% and 40% relative humidity values at 25° C. with a clear hysteresis. The presence of the hysteresis suggested a phase change from a monohydrate to an anhydrous crystalline form. This phase transition could be confirmed by a variable X-ray powder diffraction study that showed conversion of Form 1 (monohydrate) to Form 2 (anhydrous).

Physical characterization of Compound 1-dihydrochloride has confirmed the existence of two crystalline forms. The main form is the monohydrate designated Form 1 and the other form is an anhydrous form, Form 2. Dynamic vapor sorption studies have shown that under ambient conditions the monohydrated form of Compound 1-dihydrochloride is the most stable form. Only at low relative humidity levels or drying under elevated temperature and/or under vacuum the anhydrous form is observed in this study. The interconversion between the two solid forms is fast and reversible.

Example 3: Aqueous Solubility of Compound 1-Dihydrochloride Monohydrate as a Function of pH A known amount of Compound 1 was weighed directly into 5 ml vials and 1 ml of each phosphate buffer was added; the solutions obtained were kept at controlled temperature (25° C.) and magnetically stirred up to 24 hours. Aliquots of obtained suspensions or solutions were centrifuged (14000 rpm 10 minutes) and withdrawn at two predefined time points (4 hours and 24 hours) appropriately diluted and analyzed by HPLC-UV using the analytical method parameters summarized in the Table 9.

TABLE 9

| Description | Value |
| --- | --- |
| Column type | Zorbax SB-C18 |
| Column length [cm] | 15 |
| Internal diameter [cm] | 0.46 |
| Particle size [μm] | 5 |
| Mobile phase | A: 0.05% v/v TFA in water; B: 0.05% v/v TFA in acetonitrile |
| Step 1: Time-Reserv. A-Reserv. B | T = 0 min. 98% A – 2% B |
| Step 2: Time-Reserv. A-Reserv. B | T = 15 min. 2% A/ 98% B to 20.0 min. |
| Step 3: Time-Reserv. A-Reserv. B | T = 20.01 min. 98% A/ 2% B to 25.0 min. |
| Flow rate [mL/min] | 1 |
| Column temperature [° C.] | 40 |
| Detector Type | UV |
| Wavelength(nm) | 210 |
| Injection volume (μL) | 5 |

Solubility data of Compound 1-dihydrochloride monohydrate and the pH values are reported in Table 10.

TABLE 10

| Media (Phosphate Buffer) | pH (4 h) | pH (24 h) | Conc. (mg/ml) 4 hours | Conc. (mg/ml) 24 hours | Visual observation (4 hours) | Visual observation (24 hours) |
|---|---|---|---|---|---|---|
| pH 4 | 3.9 | 3.9 | >143 | 132.8 | Clear, transparent solution | The solution was transparent but a gel like precipitate was sticking to the vial |
| pH 5 | 4.9 | 4.9 | >135 | 107.0 | | |
| pH 6 | 6.2 | 6.2 | >135 | 101.6 | | |
| pH 7 | 7.1 | 7.0 | >133 | 87.8 | | The solution was yellow and a sticky precipitate can be observed |
| pH 8 | 8.1 | 8.1 | >127 | 68.3 | | |
| pH 9 | 8.7 | 8.9 | >109 | 61.4 | | |

Example 4: Physical Stability of Compound 1-Dihydrochloride

A physical stability study of Compound 1-dihydrochloride (mixture of Form 1 and Form 2) was conducted. A solid sample of Compound 1-dihydrochloride was incubated under four relative humidity and temperature conditions: 5° C./ambient RH, 25° C./60% RH, 30° C./65% RH and 40° C./75% RH. At regular intervals, the compound was analyzed by HR-XRPD and TGMS. After three days exposure, the initial crystal form of Compound 1-dihydrochloride showed full conversion to Form 1 (monohydrate) at all four conditions tested. No significant changes in the solid form were observed upon incubation for extended period of times (at least up to 1 month).

Figure 11:
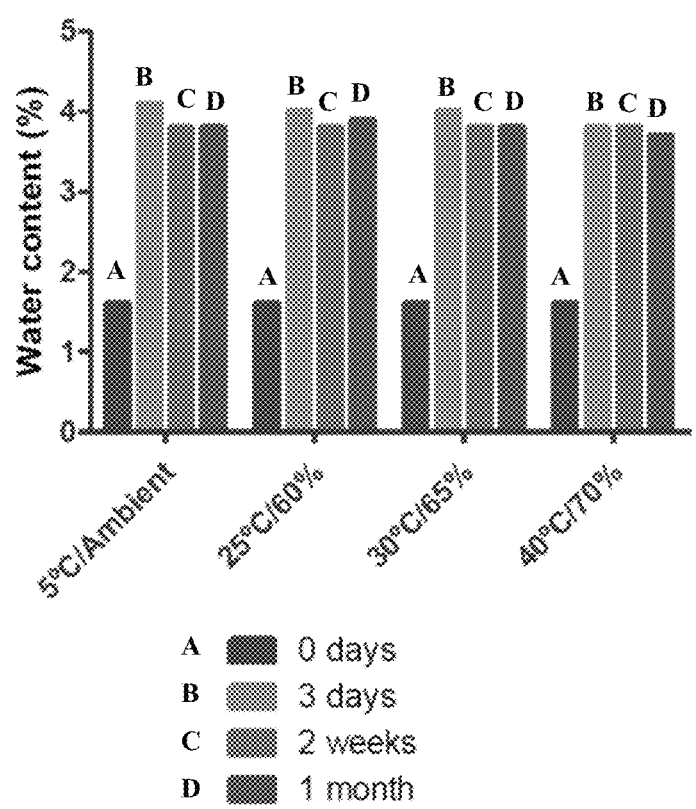
FIG. 11 shows the water content of Compound 1-dihydrochloride after incubation at different temperatures and RH conditions.

The water content of each sample was determined by TGMS analysis and is presented in FIG. 11. After 3 days exposure, the water content increased from 3.1% to values between 3.8 and 4.1% (corresponding to 1 or 1.1 molecule of water per molecule of Compound 1-dihydrochloride. The water content is in line with the monohydrate nature of Compound 1-dihydrochloride Form 1. The TGMS analyses recorded for the 2 weeks and 1-month incubation is also along the 3.8% of water (1 molecule of water per molecule of API).

This data shows that Form 1 is physically stable and non-hygroscopic under the tested conditions. No changes in the crystalline phase were observed for the samples incubated for 4 weeks. Furthermore, no significant changes in the water content were recorded upon exposure to various conditions and times.

Example 5: Polymorph Screen of Compound 1-Dihydrochloride

Generation of Compound 1-Dihydrochloride Amorphous Powder.

Approximately 20 mg of Compound 1-dihydrochloride was weighed into nine separate 1.8 mL glass vials, and nine selected solvent systems were added to these vials in steps until a clear solution was obtained. In several solvent systems (2-propanol-water, 1,4-dioxane/water, tetrahydrofuran/water, ethanol/water, acetone/water, and acetonitrile/water; all in a 90/10 v/v ratio) the API did not dissolve; therefore, these experiments were discarded. The solutions (derived from methanol/water, 90/10 v/v ratio; dimethylsulfoxide/water, 1/1 v/v ratio; and water) were frozen in liquid nitrogen followed by drying using Crys Alpha 2-4 LO for 24 hours. An extra drying at 50° C. and 5 mbar was applied for 4 hours. The resulting solids were analyzed by HT-XRPD. From one solvent, water, an amorphous solid was obtained. These conditions were scaled-up to produce 1600 mg of amorphous solid for the polymorph screen.

Polymorph Screening Experiments

The design of a comprehensive polymorph screen is characterized by utilizing different crystallization techniques combined with a variety of solvents and solvent mixtures. The diversity of a screen will depend on the solubility profile of the API. Certain crystallization modes such as equilibration of suspensions require an intermediate solubility, whereas, anti-solvent crystallization relies on solvents with good solubility and solvents with a close to zero solubility.

The polymorph screen comprised of the following crystallization modes:

Solvent equilibration at RT and 50° C. in 25 solvent systems;

Evaporative crystallization;

Cooling crystallization with hot-filtration;

Crash-crystallization using anti-solvent addition;

Crystallization by thermocycling;

Sonication;

Vapor diffusion onto solids;

Vapor diffusion into liquids.

The solids obtained from the various crystallization experiments were analyzed by High Throughput XRPD (HT-XRPD). If relevant, the mother liquors were allowed to evaporate completely, and the remaining solids were analyzed by HT-XRPD. Subsequently, all solids were exposed to accelerated aging conditions for 48 hours at 40° C. and 75% RH (AAC).

From the polymorph screen, four novel diffractograms were identified in addition to the two known forms of Compound 1-dihydrochloride, Form 1 and Form 2. Form 1 was the most abundant solid form found in this polymorph screen. The novel diffractograms were designated Forms 3, 4, 5 and 6. All these forms were found with low frequency and were poorly crystalline. They all were physically unstable as conversion to Form 1 was observed upon exposure to short term stress conditions (2 days at 40° C. and 75% RH). The HT-XRPD patterns of the new Forms 3, 4, 5 and 6 are shown in FIG. 12, FIG. 13, FIG. 14, and FIG. 15, respectively. Table 11 provides the summary of the experimental conditions under which these forms were obtained.

TABLE 11

Summary of the solid forms of Compound 1-dihydrochloride found during the polymorph screen. The physical stability of the forms was determined upon exposure to 40° C. and 75% RH for 2 days (AAC).

| Form | Physical stability upon exposure to AAC | Crystallization conditions | Crystallization solvents |
|---|---|---|---|
| 1 | Stable | — | — |
| 2 (with traces of Form 1) | Converted to Form 1 | Solvent equilibration 50° C. | 1,2-Dimethoxyethane, DMF, DMA, DMSO/DCM (5/95), DMSO/MTBE (5/95), DMA/toluene (5/95), DMSO/anisole (75/25), NMP/THF (50/50), THF/water (80/20) |
|  |  | Thermocycling | NMP/THF (50/50), DMSO/anisole (25/75) |
|  |  | Anti-solvent | Water (S), THF (AS) |
| 3 | Converted to Form 1 | Solvent equilibration RT (wet solid) | iso-Amyl alcohol |
| 4 | Converted to Form 1 | Solvent equilibration RT (wet solid) | TFE |
|  |  | Cooling crystallization | TFE |
|  |  | Hydrate screen | Water/IPA (2.6/97.4) |
| 5 | Converted to Form 1 | Solvent equilibration RT (dried solid) | iso-Amyl alcohol |
|  |  | Solvent equilibration 50° C. | iso-Amyl alcohol |
|  |  | Hot-filtration | Chloroform/isopropyl acetate (50/50) |
| 6 | Converted to Form 1 | Solvent equilibration 50° C. | 1,2-Dimethoxyethane, DMSO/DCM (5/95), DMF/anisole (5/95) |
|  |  | Cooling crystallization | Ethanol/p-xylene (50/50) |
|  |  | Evaporative crystallization | 1-Propanol |
|  |  | Hydrate screen 35° C. & 50° C. | Water/IPA (0.7/99.3, 2.6/97.4) |

(S) indicates solvent,
(AS) indicates anti-solvent.
All ratios are volume/volume ratios.

All above mentioned forms except for Form 3 were further analyzed by DSC, TGMS, and HPLC. A short description of the analytical characterization is presented below.

Form 3 was obtained as a pure crystalline phase in a single experiment. No further analysis could be done on this form due to the limited physical stability. This form was found in the solid obtained from iso-amyl alcohol after being dried under ambient condition. Upon drying under vacuum, conversion to Form 1 occurred. Also, upon exposure to short term stress conditions Form 3 transformed into Form 1.

Form 4 was found in a few crystallization experiments performed in TFE, 1,4-dioxane and IPA/water. The thermal analysis confirmed that Form 4 is a mixed solvated/hydrated form. Based on the different solvent/water contents determined for several Form 4 samples, we assumed that Form 4 is a class of isostructural mixed hydrate/solvates.

A mixed hydrated/iso-amyl alcohol solvated form was identified from the solvent equilibration experiments performed in iso-amyl alcohol. This new solid form was designated Form 5 which seemed to be physically stable upon drying under vacuum; however, upon exposure to AAC conversion to Form 1 was observed.

Form 6 was predominately found during the hydrate screen experiments performed in IPA/water mixtures but also it was identified in a few solvent equilibration experiments performed in different solvents, such as 1,2-dimethoxyethane, DMSO/DCM and DMF/anisole. Form 6 was mainly found from the solids dried under vacuum; however, conversion to Form 1 was observed after AAC. The analytical characterization suggested that Form 6 is a mixed hydrated/solvated form. Based on the different solvents that can be incorporated to the structure of Form 6 we assumed that this form is clustering a class of isostructural mixed hydrate/solvates containing different organic solvent molecules.

Hydrate Screen

Solvent equilibration experiments were performed in several water/organic solvents mixtures to investigate the formation of other hydrated forms. Suspensions of amorphous Compound 1-dihydrochloride were prepared in 15 water/solvent mixtures with different water activities. The suspensions were stirred for 7 days at 5° C., 20° C., 35° C. and 50° C.

After completion of the equilibration time, the remaining solids were analyzed by HT-XRPD dry under ambient conditions and dried under vacuum. The mother liquors were analyzed by Karl Fisher titration for water content determination. Three experiments did not show solids after the equilibration conditions. The solutions from these experiments were evaporated under vacuum (200 mBar) and the obtained dried solids analyzed by HT-XRPD. All the solids were then exposed to 40° C. and 75% RH for two days.

From most of the crystallization conditions, the monohydrate Form 1 had crystallized.

From IPA/water mixtures, Form 4, Form 6 and mixtures of those with Form 1 were identified at low water contents (<5%). At water activity values above 0.5, the monohydrated Form 1 was identified in all cases. Based on the analytical characterization, Form 4 and 6 seemed to be mixed hydrated/solvated forms which upon exposure to short term stress conditions converted to Form 1.

The solvent equilibration experiments performed in ethyl acetate/water showed differences in the solid form assessed to the solids dried under ambient and under vacuum. Form 1 was identified in most of the solids dried under ambient conditions. Upon drying under vacuum, mixtures of Form 1 and 2 were identified. Form 6 was identified in mixture with Form 1 at water activity values below 0.3 at temperatures above 35° C. The presence of Form 2 was observed when elevated temperatures and high-water contents were used but also at temperatures below 20° C. and low water contents.

Similar trend was observed for the experiments performed in acetonitrile/water. All the solids dried under ambient conditions were attributed to Form 1. Upon drying the solids under vacuum, in some cases partial conversion to Form 2 was observed. This observation was noticed for the solvent equilibration experiments performed at temperatures above 35° C. The experiments performed below 25° C. did not show any solid form conversion upon drying.

The physical stability study performed for 2 days at 40° C./75% RH led to the identification of Form 1. All new powder patterns detected in this study showed conversion to the initial Form 1.

Example 6: Stability of Combination Formulation

The stability of aqueous solutions of Compound 1-dihydrochloride in combination with meropenem at pH 5.0 vs of Compound 1-dihydrochloride in combination with cefepime at pH 5.0 after 24 hours was studied. The results are shown in Table 12

TABLE 12

| Solution composition | % present at pH 5.0 at 25° C. Time elapsed | | |
|---|---|---|---|
| | 24 hours Compound 1 | 24 hours meropenem | 20 hours cefepime |
| Compound 1 | 100 | — | — |
| Meropenem | — | 89 | — |
| cefepime | — | — | 99 |
| Compound 1 + meropenem | 57 | 20 | — |
| Compound 1 + cefepime | 99.9 | — | 99.1 |

Example 7: Efficacy of Combination Formulation

The results shown in examples 7A-7D show that the cefepime/Compound 1 combination is more efficacious than the meropenem/Compound 1 combination against a variety of organisms.

Example 7A: *Elizabethkingia meningoseptica*

*Elizabethkingia meningoseptica* is a Gram negative rod that expresses 2 chromosomal metallo-beta-lactamase (both carbapenemases) and a class A serine cephalosporinase CME (AAC, 2012, 1686-1692). The MIC testing results (N=10 strains) are shown in Table 13.

TABLE 13

| Compounds | Range | $MIC_{50}$ (µg/mL) | $MIC_{90}$ (µg/mL) | % S@8 |
|---|---|---|---|---|
| Cefepime | 16-32 | 16 | 32 | 0 |
| Cef/Compound 1@4 | 2-8 | 4 | 4 | 100 |
| Meropenem | 16-128 | 64 | 128 | 0 |
| Mero/Compound 1@4 | 4-16 | 8 | 16 | 70 |

Example 7B: *Stenotrophomonas maltophilia*

*Stenotrophomonas maltophilia* is a Gram negative bacillus. It is an opportunistic MDR pathogen. It has been linked to infections with high morbidity and mortality in severely immunocompromised and debilitated individuals. The MIC testing results are shown in Table 14.

TABLE 14

| Compounds | Range | $MIC_{50}$ (µg/mL) | $MIC_{90}$ (µg/mL) | % S |
|---|---|---|---|---|
| Cefepime | 1-128 | 32 | 64 | 20 |
| Cef/Compound 1@4 | 0.5-16 | 4 | 16 | 80 |

TABLE 14-continued

| Compounds | Range | $MIC_{50}$ (µg/mL) | $MIC_{90}$ (µg/mL) | % S |
|---|---|---|---|---|
| Meropenem | 64->128 | 128 | >128 | 0 |
| Mero/Compound 1@4 | 16->128 | 64 | >128 | 0 |

Example 7C: *Pseudomonas aeruginosa*

507 isolates non-susceptible to meropenem (MIC values to meropenem>8 µg/mL). The MIC testing results are shown in Table 15.

TABLE 15

| Compounds | Range | $MIC_{50}$ (µg/mL) | $MIC_{90}$ (µg/mL) | % S@8 |
|---|---|---|---|---|
| Cefepime | 1-128 | 32 | 256 | 30.8 |
| Cef/Compound 1@4 | 1->64 | 8 | >64 | 60 |
| Meropenem | 16->128 | 32 | >128 | 0 |
| Mero/Compound 1@4 | 16->128 | 16 | 64 | 23.9 |

Example 7D: *Pseudomonas aeruginosa*

554 isolates non-susceptible to cefepime (MIC values to cefepime>8 µg/mL). The MIC testing results are shown in Table 16.

TABLE 16

| Compounds | Range | $MIC_{50}$ (µg/mL) | $MIC_{90}$ (µg/mL) | % S@8 |
|---|---|---|---|---|
| Cefepime | 16->512 | 32 | 256 | 0 |
| Cef/Compound 1@4 | <0.06->64 | 8 | >64 | 55.8 |
| Meropenem | <0.12->128 | 16 | >128 | 36.6 |
| Mero/Compound 1@4 | <0.06->64 | 8 | 64 | 52 |

Example 8: A Randomized, Drug-Drug Interaction Study to Assess the Safety and Pharmacokinetics of Compound 1 in Healthy Adult Volunteers

Example 8A: Phase 1 Clinical Study Overview

Example 8 describes four Phase 1 clinical studies designed to evaluate the safety, tolerability and PK of various dose-levels of Compound 1 when administered as single or multiple doses either alone or in combination with cefepime comprising the following components (and outlined in Table 17):
1) Single ascending (SAD) and multiple ascending (MAD) doses of Compound 1 in healthy volunteers; and
2) Single dose drug-drug interaction of Compound 1, cefepime and metronidazole alone and of Compound 1 combined with cefepime with and without metronidazole (Part 1), and 10-day repeated doses of Compound 1 combined with cefepime (Part 2) in healthy volunteers.

TABLE 17

| Study Objective(s) | Study Design | Dosage Regimens | No. of Subjects | Treatment Duration |
|---|---|---|---|---|
| Safety, tolerability, and | Two-part, randomized, | Part 1: Single ascending doses of | Part 1: 6 test drug and 2 placebo at | Single dose |

TABLE 17-continued

| Study Objective(s) | Study Design | Dosage Regimens | No. of Subjects | Treatment Duration |
|---|---|---|---|---|
| PK in healthy adult volunteers | double-blind, placebo-controlled | 62.5, 125, 250, 500, 1000 and 1500 mg Compound 1 or placebo. Includes QT concentration-effect modeling. | each dose level | |
| | | Part 2: Multiple ascending doses of 250, 500 and 750 mg Compound 1 or placebo as a 2 hr IV infusion q8h | Part 2: 9 test drug and 3 placebo at each dose level | 10 days |
| DDI; Safety, tolerability, and PK in healthy adult volunteers | Two-part, randomized, three-way crossover drug-drug interaction study | Part 1: Single doses of 750 mg of Compound 1 alone, 2 g cefepime alone, 500 mg metronidazole alone or Compound 1 in combination with cefepime with and without metronidazole | Part 1:18 subjects | Single dose in each of 5 dosing periods |
| | | Part 2: Cefepime 2 g with Compound 1 500 mg or 750 mg as a 2 hr IV infusion q8h for 10 days | Part 2: 24 subjects (10 subjects/dose level) and 4 placebo subjects | 10 days |

Abbreviations:
~ = approximately;
BAT = Best available therapy;
DDI = drug-drug interaction;
hr = hour;
IV = intravenous;
PK = pharmacokinetics;
q8h = three times daily, 8 hours apart;
TBD = to be determined Compound 1 Human Pharmacokinetic and Pharmacokinetic/Pharmacodynamic Target Attainment Estimates The results from in vitro and in vivo nonclinical PK/PD studies, the human PK data collected in the Phase 1 Study, and human plasma binding data were used to determine human therapeutic doses required for PK/PD target attainment. In vitro studies have demonstrated that human serum protein binding of Compound 1 is 37%, leaving a free fraction of 63%. Table 18 summarizes the calculated values for the total $AUC_{0-24}$, the corresponding free fraction ($fAUC_{0-24}$) and the $fAUC_{0-24}$/MIC ratio estimates based on the established CLSI breakpoint for cefepime of 8 mg/L, when administered at a 2 g dose tid.

TABLE 18

| Dose Level (q8 hr) | Total $AUC_{0-24}$ (hr*mg/L) | $fAUC_{0-24}$ (hr*mg/L) | $fAUC_{0-24}$/MIC Ratio (for MIC = 8 mg/L) |
|---|---|---|---|
| 250 | 123 | 77 | 9.7 |
| 500 | 248 | 156 | 19.5 |

Abbreviations: :
$AUC_{0-24}$ = area under the plasma concentration versus time curve from time zero to 24 hours;
$fAUC_{0-24}$ = free drug area under the plasma concentration versus time curve from time zero to 24 hours;
MIC = minimum inhibitory concentration;
q8 hr = every 8 hours The $fAUC_{0-24}$/MIC ratios (based on an MIC value of 8 mg/L) for all doses≥250 mg q8 hr exceed the PK/PD target required to achieve bacterial stasis for the isolates studied to date. Similarly, the $fAUC_{0-24}$/MIC values for doses of approximately 375 mg q8 hr (interpolated from shown data) exceed the $fAUC_{0-24}$/MIC ratios required to achieve 1 log of bacterial killing. Based on these data, a dose of 500 mg q8 hr provides approximately three times the drug exposure required for PK/PD target attainment for bacterial stasis.

Protocol Summary

Population:
  42 subjects overall divided between two study parts as follows:
  Part 1: Single-Dose 5-Period Cross-Over: 18 healthy male and female subjects
  Part 2: 10-Day randomized Repeat-Dose: 24 healthy male and female subjects Inclusion Criteria No exemptions will be granted for Inclusion/Exclusion criteria. The following inclusion criteria must be met for a subject to be eligible for inclusion in the study:
  1. Willing to participate in the study, willing to give written informed consent, and comply with the study restrictions
  2. Gender: male, or female with a negative serum pregnancy test (β-human chorionic gonadotropin[β-hCG]) at screening and Day −1; females may be of childbearing potential or of non-childbearing potential
  3. Age: 18-55 years, inclusive, at screening
  4. Weight: ≥50 kg
  5. Body mass index (BMI): ≥18.5 kg/m2 and <30.0 kg/m2
  6. Normal blood pressure, defined as a systolic value≥90 mm Hg and ≤140 mm Hg and a diastolic value less than 90 mm Hg (Screening and Day −1). Values outside the range for inclusion may be retested once if there is a clinical rationale for the out of range value.
7. Urine dipstick results for protein are negative or trace at screening and Day −1.
8. All values for hematology and clinical chemistry tests of blood and urine are either within the normal range or defined as permitted exceptions in Table 3 at screening and Day −1. Values not within these ranges may be retested once if there is a clinical rationale for the out of range value. Screening labs are defined in Table 9 and Table 10.
9. Ability and willingness to abstain from alcohol, from 48 hours (2 days) prior to admission to the clinical research center until the follow-up visit.
10. Males who are not surgically sterilized and females of childbearing potential must agree to use highly effective methods of contraception during the study and for 90 days after the last dose of Study Medication. A woman is considered of childbearing potential unless post-menopausal (≥1 year without menses) or surgically sterilized via bilateral oophorectomy, hysterectomy, bilateral tubal ligation or successful Essure® placement with a documented confirmation test at least 3 months after the procedure.
Highly effective contraception is defined as a method of contraception that has a <1% failure rate when used consistently and correctly. These methods are:
Hormonal contraceptives (e.g., combined oral contraceptives, patch, vaginal ring, injectables, and implants);
Intrauterine device (IUD) or intrauterine system (IUS);
Double barrier methods of contraception (e.g., male condom with diaphragm, male condom with cervical cap)
Monogamous relationship with a vasectomized partner,
Total abstinence, in accordance with the lifestyle of the subject.
11. All over-the-counter [OTC] medication, health supplements, and herbal remedies (e.g., St. John's Wort extract) must have been stopped at least 14 days prior to admission to the clinical research center. An exception is made for acetaminophen, which is allowed at doses≤3 g daily up to admission to the clinical research center.
12. Suitable veins for cannulation/multiple venipunctures as assessed by the Investigator at screening.

Exclusion Criteria

A subject who meets any of the following exclusion criteria will not be eligible for inclusion in the study:
1. Employee of Sponsor or Principal Investigator
2. Female who is pregnant, lactating, or planning to attempt to become pregnant during this study or within 90 days after dosing of study medication.
3. Male with a female partner who is pregnant or lactating during this study, or planning to attempt to become pregnant during this study or within 90 days after dosing of study medication.
4. Use of any investigational drug or device within 30 days prior to screening (90 days for an injectable biological agent).
5. Presence of a congenital or acquired immunodeficiency syndrome.
6. Presence of current cardiovascular, respiratory, hepatic, renal, gastrointestinal, endocrine, autoimmune, hematologic, neoplastic, or neurologic disorders.
7. Any disease that, in the opinion of the Investigator, poses an unacceptable risk to the subjects.
8. Clinically significant ECG abnormality, defined as a Mean QTcF of ≥450 msec, a short QTcF (<300 msec), or ECG evidence of atrial fibrillation, atrial flutter, complete right or left bundle branch block, Wolff-Parkinson-White syndrome, or cardiac pacemaker (Screening or Day −1).
9. Current or previous history of second and third degree heart block and/or clinically relevant prolongation of the PR interval as determined by the Investigator (Screening or Day −1).
10. History of drug allergy of a severity that required urgent medical treatment, such as treatment with epinephrine in an Emergency Department.
11. History of any hypersensitivity reaction following administration of a cephalosporin, penicillin or other beta-lactam antibacterial drug.
12. History of hypersensitivity to metronidazole or other nitroimidazole derivatives.
13. Requires regular use of a medication for a chronic condition or has taken prescription medication or received a vaccination within 14 days prior to Day −1. Hormonal contraceptives are permitted.
14. Use of >3 grams of acetaminophen on 3 or more days in the 14 days prior to screening
15. Strenuous activity, sunbathing, and contact sports within 48 hours (2 days) prior to admission to the clinical research center and for the duration of the study.
16. History of donation of more than 450 mL of blood within 60 days prior to dosing in the clinical research center or planned donation before 30 days has elapsed since final dose of study medication.
17. Plasma or platelet donation within 7 days of dosing and throughout the entire study.
18. Current suspected drug or alcohol abuse as specified in the Diagnostic and Statistical Manual of Mental Disorders, Fifth Edition, Text Revision criteria.
19. Recent history of alcohol consumption exceeding 2 standard drinks per day on average (1 standard drink=10 grams of alcohol).
20. Positive alcohol or drug test result at screening or Day −1.
21. Positive screening test for hepatitis B surface antigen (HBsAg), anti-hepatitis C virus (HCV) antibodies, or anti-human immunodeficiency virus (HIV) 1 and 2 antibodies.
22. Temperature>38.5° C. or acute illness on admission (Day −1).
23. Previous participation in a study of Compound 1.

Investigational Products

Identity of Investigational Product(s) and Placebo
Compound 1 was provided in glass vials containing 500 mg of a freeze dried solid. Compound 1 was reconstituted at the site with sterile water for injection. The site obtained the following products from a commercial pharmacy or wholesaler:
Cefepime for IV infusion
Metronidazole 500 mg immediate release tablets
Sodium chloride Injection United States Pharmacopeia (USP) 0.9%
Water for Injection.

Objectives

Part 1:

Primary:
- To evaluate the pharmacokinetics (PK) of Compound 1 and cefepime following single doses alone and in combination (Part 1A).

Secondary:
- To evaluate the PK of metronidazole PK following single doses of metronidazole alone and in combination with Compound 1 and cefepime (Part 1B).
- To evaluate the PK of Compound 1 and cefepime PK following single doses of co-administered Compound 1 and cefepime when co-administered with metronidazole (Part 1B).
- To evaluate the safety and tolerability of a single dose of Compound 1 combined with cefepime, with and without metronidazole in comparison to stand-alone Compound 1, cefepime, and metronidazole in healthy adult volunteers.

Part 2:

Primary
- To evaluate the safety and tolerability of repeated dose (10 days) of two dose levels of Compound 1 combined with cefepime in healthy adult volunteers Secondary:
- To evaluate Compound 1 and cefepime plasma-trough concentrations with repeated doses (10 days) of two dose levels of Compound 1 co-administered with cefepime in healthy adult volunteers.

Exploratory:
- To evaluate serum and urine bactericidal activity at peak and trough concentrations.

Study Design

This is a Phase 1, randomized, single-center, drug-drug interaction study in healthy adult male and female volunteers. The study consisted of two independent parts. Each part enrolled separate groups of subjects. Eligible subjects were allowed to participate in either Part 1 or Part 2, but not both.

Part 1

Part 1 enrolled 18 subjects into randomized, single dose assessment of five treatments with a sequential 3-period crossover (Part 1A) and 2-period crossover (Part 1B) design. Subjects who had not met any halting rules in Part 1A were eligible for re-randomization into Part 1B.

Part 2

Part 2 enrolled 24 subjects into a randomized, double-blind assessment of three treatments in a parallel group design.

Rationale

In view of the available nonclinical data, and data from single and multiple dose administration in humans, further development of Compound 1 in combination with a β-lactam antibiotic was warranted. This study provided an assessment of the safety and pharmacokinetics of Compound 1 combined with cefepime with and without metronidazole in a multi-period single dose cross-over design in Part 1, and of the safety, tolerability, and pharmacokinetics (PK) of multiple doses of Compound 1 administered in combination with cefepime in Part 2.

Compound 1 was administered as an intravenous (IV) infusion over 2 hours.

Subject Selection Rationale

Due to the study design, the low risk of clinically significant toxicity at anticipated exposure levels, and the absence of any potential therapeutic benefit, healthy subjects were chosen for this study population. Moreover, use of healthy subjects as opposed to patients allowed a clearer interpretation of the study results, as there was no confounding factors resulting from changes in disease state and/or concomitant medications.

Example 8B: Part 1 of Multiple Dose Study

Part 1A

All treatments in Part 1A were administered as a single 2-hour IV infusion and included the treatments in Table 19. All subjects received all three treatments. Dosing occured on Day 1, Day 4, and Day 7. The sequence of administration was randomized.

The Part 1A treatment descriptions are in Table 19.

TABLE 19

| Treatment | Treatment Description |
|---|---|
| A | 750 mg Compound 1 |
| B | 2 g cefepime |
| C | 750 mg Compound 1 + 2 g cefepime |

Part 1B

Part 1B included two treatments, which were administered according to the treatment sequence specified in the randomization code. Dosing occured on Day 10 and Day 13. Treatments are described in Table 20.

TABLE 20

| Treatment | Treatment Description |
|---|---|
| D | metronidazole 500 mg + Compound 1 750 mg + cefepime 2 g |
| E | metronidazole 500 mg + 2 g cefepime |

Study Notes:
- Each treatment period repeated the specified assessments.
- Subjects were discharged after completion of all Day 15 assessments.
- If a subject withdrew from the study prior to Day 15, all ET assessments was completed at the time of discontinuation. A scheduled assessment collected within 1 day of ET may have been used in place of an ET assessment.
- Additional general or symptom directed examinations may have been performed at other time points, at the discretion of the Principal Investigator.
- Screening included height, weight, and BMI calculation. Day −1 includes weight and BMI calculation.
- Clinical laboratory included serology (HBsAg, anti-HCV, and anti-HIV 1 and 2 antibodies) at screening.
- PK samples were collected prior to each treatment administration and at 0.5, 1, 2 (end of infusion), 2.25, 2.5, 3, 4, 6, 8, 12, 16, 24, 36 and 48 hours after the start of the infusion.

Adverse events (AEs) were collected from admission (Day −1) until completion of the follow-up visit. Any AEs continuing at follow-up were followed until resolution or stabilization.

Subjects received one dose of the assigned randomized treatment on Days 1, 4, 7, 10, and 13. All subjects received all treatments in a prespecified order according to the randomization schedule. Compound 1 and cefepime were administered IV. Metronidazole was administered orally.

Included FSH level at Screening in post-menopausal females.

Example 8C: Part 2 of Multiple Dose Study

In Part 2, subjects were randomized in a 5:5:2 ratio to one of the three treatments in Table 21.

TABLE 21

| Treatment | Treatment Description |
|---|---|
| 2A | 500 mg Compound 1 + 2 g cefepime |
| 2B | 750 mg Compound 1 + 2 g cefepime |
| 2C | Placebo (matching Compound 1 + cefepime) |

Treatment was administered every 8 hours (q8h) as 2-hour IV infusion for 10 days. Subjects received a total of 28 doses with a single dose administered on Day 10.

Subjects were discharged after review of Day 10 labs and ECG and completion of all Day 11 assessments.

If a subject withdrew from the study prior to Day 11, ET assessments were completed at the time of discontinuation for subjects who did not have assessments performed after their final dose of study medication.

Subjects who discontinued were to complete the follow-up visit 7 days (±1 day) after the last dose of study medication.

Additional general or symptom directed examinations may have been performed at other time points, at the discretion of the Principal Investigator.

Height and BMI calculation at screening only. Body weight at screening and on Day −1 (admission).

ECGs on Days 1 and 10 completed following administration of the first infusion of the day.

Vital signs include supine systolic and diastolic blood pressure, pulse, body temperature, and respiratory rate. On Days 1-9, vitals were collected before and 2 hours after the start of the first infusion of the day. On Day 10, vitals were collected prior to and after dosing (at any time).

Study medication was administered as a 2-hour intravenous infusion every 8 hours (total of 28 doses with last dosing in the morning of Day 10).

Samples were collected before each dose on Days 1 and 2, and before the morning dose on Days 3, 5, and 10.

Blood samples were collected on Day 1 pre-dose, and on Day 10 at the end of infusion and 8 hours after the start of infusion. Urine samples were collected on Day 1 pre-dose (single sample within 12 hours of dosing), and on Day 10 as pooled collections of all urine for the intervals 0-4 and 4-8 hours after the start of the infusion.

AEs were collected from admission (Day −1) until completion of the follow-up visit. Any AEs continuing at follow-up were followed until resolution or stabilization.

Included FSH level at Screening in post-menopausal females.

Results

There was no significant difference in the pharmacokinetic parameters of $AUC_{(0-inf)}$ and $C_{max}$ for Compound 1 or cefepime upon co-administration of the two drugs relative to administration of either drug alone.

There was no meaningful pharmacokinetic interaction between metronidazole and cefepime/Compound 1 relative to administration of metronidazole alone or the cefepime/Compound 1 combination without metronidazole.

Both single and repeat doses of study medication were well-tolerated. There were no clinically significant vital sign, ECG or laboratory abnormalities. All adverse events were mild in intensity.

Example 9: Treatment of Bacterial Infection with Cefepime and Compound 1 Combination Therapy Subjects with infections at multiple anatomic sites caused by resistant pathogens including lower respiratory tract infections, complicated intra-abdominal infections (cIAI) and complicated urinary tract infections (cUTI), such as Pyelonephritis, are administered a combination of cefepime/Compound 1 as follows in Table 22.

TABLE 22

| Dosage Regimens | Subject Population | Treatment Duration |
|---|---|---|
| Compound 1 500 mg in combination with cefepime 2 g IV q8h | patients with cUTI | 5-14 days |
| Compound 1 500 mg in combination with cefepime 2 g IV q8h | patients with cIAI | 5-14 days |
| Compound 1 500 mg in combination with cefepime 2 g IV q8h | patients infected with resistant pathogens at multiple sites | 5-14 days |
| Compound 1 750 mg in combination with cefepime 2 g IV q8h | patients with cUTI | 5-14 days |
| Compound 1 750 mg in combination with cefepime 2 g IV q8h | patients with cIAI | 5-14 days |
| Compound 1 750 mg in combination with cefepime 2 g IV q8h | patients infected with resistant pathogens at multiple sites | 5-14 days |

Abbreviations:
~ = approximately;
cIAI = complicated intra-abdominal infection;
cUTI = complicated urinary tract infection;
hr = hour;
IV = intravenous;
q8h = three times daily, 8 hours apart;

Treatments in Table 22 are administered every 8 hours (q8h) as 2-hour IV infusion for 10 days. Subjects will receive a total of 28 doses with a single dose administered on Day 10.

What is claimed is:

1. A pharmaceutical composition comprising:
   (i) (R)-3-(2-(trans-4-(2-aminoethylamino)cyclohexyl)acetamido)-2-hydroxy-3,4-dihydro-2H-benzo[e][1,2]oxaborinine-8-carboxylic acid:

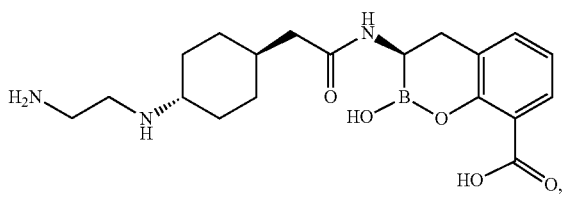 [SMILES: NCCN[C@H]1CC[C@H](CC(=O)N[C@H]2Cc3cccc(C(=O)O)c3OB2O)CC1]

or a pharmaceutically acceptable salt, a solvate, or a pharmaceutically acceptable salt and solvate thereof;
(ii) cefepime; and
(iii) L-arginine.

2. The pharmaceutical composition of claim 1, wherein the pharmaceutical composition is formulated as a homogeneous liquid suitable for injection.

3. The pharmaceutical composition of claim 2, further comprising an aqueous carrier.

4. The pharmaceutical composition of claim 3, wherein the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof.

5. The pharmaceutical composition of claim 2 having a pH from about 4 to about 9.

6. The pharmaceutical composition of claim 2 having a pH from about 4 to about 6.

7. The pharmaceutical composition of claim 1, wherein the pharmaceutical composition is formulated as a powder for reconstitution.

8. The pharmaceutical composition of claim 7, wherein the pharmaceutical composition is suitable for injection once reconstituted with an aqueous carrier.

9. The pharmaceutical composition of claim 8, wherein the aqueous carrier is water for injection, 0.9% sodium chloride injection, 5% dextrose injection, 10% dextrose injection, sodium lactate injection, 5% dextrose and 0.9% sodium chloride injection, lactated Ringers and 5% dextrose injection, sodium chloride/sodium acetate/sodium gluconate/potassium chloride/magnesium chloride injection, sodium chloride/potassium acetate/magnesium acetate in 5% dextrose injection, or any combinations thereof.

10. The pharmaceutical composition of claim 1, wherein (R)-3-(2-(trans-4-(2-aminoethylamino)cyclohexyl) acetamido)-2-hydroxy-3,4-dihydro-2H-benzo[e][1,2]oxaborinine-8-carboxylic acid or a pharmaceutically acceptable salt, a solvate, or a pharmaceutically acceptable salt and solvate thereof is (R)-3-(2-(trans-4-(2-aminoethylamino)cyclohexyl) acetamido)-2-hydroxy-3,4-dihydro-2H-benzo[e][1,2]oxaborinine-8-carboxylic acid dihydrochloride.

11. The pharmaceutical composition of claim 1, wherein the pharmaceutical composition comprises about 500 mg of (R)-3-(2-(trans-4-(2-aminoethylamino)cyclohexyl) acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

12. The pharmaceutical composition of claim 1, wherein the pharmaceutical composition comprises about 750 mg of (R)-3-(2-(trans-4-(2-aminoethylamino)cyclohexyl) acetamido)-2-hydroxy-3,4-dihydro-2H-benzo[e][1,2]oxaborinine-8-carboxylic acid, a pharmaceutically acceptable salt, a solvate, or a pharmaceutically acceptable salt and solvate thereof.

13. The pharmaceutical composition of claim 1, wherein the pharmaceutical composition comprises about 2 g of cefepime.

14. A method of treating a bacterial infection in a subject in need thereof, comprising administering to the subject a pharmaceutical composition of claim 1.

15. The method of claim 14, wherein the pharmaceutical composition is administered by intravenous (IV) infusion.

* * * * *